United States Patent
Balazovsky et al.

(10) Patent No.: US 8,575,382 B2
(45) Date of Patent: Nov. 5, 2013

(54) LOW MOLECULAR WEIGHT PHARMACOLOGICAL ACTIVITY MODULATORS

(75) Inventors: Mark Borisovich Balazovsky, St. Petersburg (RU); Viktor Georgievich Antonov, Vsevolozhsk (RU); Alexandr Nikolaevich Belyaev, St. Petersburg (RU); Alexei Vladimirovich Eremin, St. Petersburg (RU)

(73) Assignee: "Ivy Pharm" LLC, St. Petersburg (RU)

( * ) Notice: Subject to any disclaimer, the term of this patent is extended or adjusted under 35 U.S.C. 154(b) by 0 days.

(21) Appl. No.: 13/383,646

(22) PCT Filed: Jul. 12, 2010

(86) PCT No.: PCT/RU2010/000391
§ 371 (c)(1), (2), (4) Date: Mar. 19, 2012

(87) PCT Pub. No.: WO2011/008132
PCT Pub. Date: Jan. 20, 2011

(65) Prior Publication Data
US 2012/0202764 A1    Aug. 9, 2012

(30) Foreign Application Priority Data
Jul. 13, 2009 (RU) .................................. 2009126459

(51) Int. Cl.
*C07F 15/00* (2006.01)
*C10L 1/30* (2006.01)

(52) U.S. Cl.
USPC ............................................ 556/146; 556/31

(58) Field of Classification Search
USPC .................................................. 556/31, 146
See application file for complete search history.

(56) References Cited

U.S. PATENT DOCUMENTS

| | | | |
|---|---|---|---|
| 5,041,580 A | 8/1991 | Miyamoto et al. | |
| 2008/0085882 A1 | 4/2008 | Siede et al. | |
| 2011/0105419 A1 | 5/2011 | Balazovsky et al. | |

FOREIGN PATENT DOCUMENTS

| CN | 1634018 | 7/2005 |
|---|---|---|
| CN | 101113155 | 1/2008 |
| FR | 2 676 648 | 5/1991 |
| GB | 1 556 204 | 11/1979 |
| JP | 5-163152 | 6/1993 |
| MD | 2861 F1 | 9/2005 |
| RU | 2144374 | 1/2000 |
| RU | 2233286 | 7/2004 |
| SU | 740790 | 6/1980 |
| WO | WO 00/50431 | 8/2000 |
| WO | WO 03/054145 | 7/2003 |
| WO | WO 2007/110745 | 10/2007 |
| WO | WO 2008/120690 | 10/2008 |
| WO | WO 2008/147243 | 12/2008 |
| WO | WO 2009/104988 | 12/2009 |

*Primary Examiner* — Johann R Richter
*Assistant Examiner* — Kofi Adzamli
(74) *Attorney, Agent, or Firm* — McCarter & English, LLP; Steven G. Davis

(57) ABSTRACT

Claimed are a compound of the general formula (I) and pharmaceutically acceptable salts thereof, where M signifies metal atoms selected independently from the group comprising Pd, Fe, Mn, Co, Ni, Cu, Zn and Mo; $R^1$ and $R^2$, independently of each other, signify hydrogen, amino, hydroxy, oxy, carboxy, cyano, $C_{1-12}$alkyl, $C_{2-12}$alkenyl, $C_{2-12}$alkynyl, $C_{1-12}$alkoxy, $C_{1-12}$alkylamino, $C_{1-12}$alkoxycarbonyl, $C_{1-12}$alkylamido, arylamido, wherein the alkylene groupings in the given substituents can in turn be substituted by one or more of the following groups: hydroxy, oxy, carboxy, amino or amido; $R^3$-$R^{10}$, independently of each other, signify hydrogen; or $NHR^3R^4$ and $NHR^5R^6$, taken together, and/or $NHR^7R^8$ and $NHR^9R^{10}$, taken together, are a ligand (or ligands) containing one or several donor aliphatic or aromatic atoms of nitrogen and being in cis position on the metal atoms (M). The claimed compound can be used in a preparation containing a coordination compound and free molecules of an aliphatic thiol (or derivatives thereof), which are not bound to the coordination compound. The coordination compound and the free molecules of an aliphatic thiol (or derivatives thereof) in the preparation can be in either cationic or anionic form or in the form of neutral particles. The proposed substances are capable of making the action of drugs more effective by increasing the affinity of the target to the drug and/or providing for therapeutically optimal concentrations of the drug in the microenvironment of the target and/or reducing the toxicity of drugs.

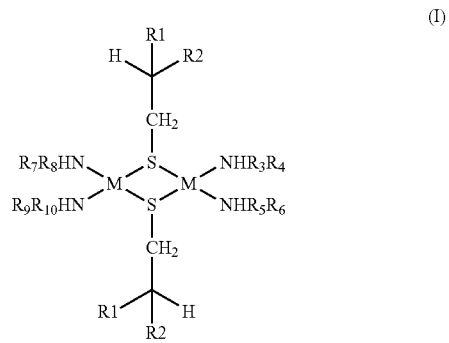

19 Claims, No Drawings

LOW MOLECULAR WEIGHT PHARMACOLOGICAL ACTIVITY MODULATORS

RELATED APPLICATIONS

This application is a U.S. national phase application of International Application No. PCT/RU2010/000391, filed Jul. 12, 2010, which claims priority to Russian Federation Patent Application No. 2009126459, filed Jul. 13, 2009. The entire teachings of the above-referenced applications are incorporated herein by reference.

FIELD OF THE INVENTION

The present invention relates to the field of the production of drug preparations and may be utilized in pharmacology, medicine and veterinary science.

PRIOR ART

Methods for improving the effectiveness of drugs include optimizing the pharmacokinetics and/or the pharmacodynamics thereof and/or reducing the toxicity thereof by chemical modification of the drug molecule and/or combined use with another chemical compound or compounds.

A chemical compound or compounds used in pharmacological solutions may or may not possess intrinsic pharmacologically significant activity, but must necessarily ensure implementation of the effect of the drug either by increasing the selectivity of the action thereof solely on its pharmacological targets and/or by providing the necessary and sufficient concentrations in the microenvironment of the biological target structures and/or by reducing the toxicity.

Thus a number of pharmacological solutions are known, including Amoxiclav, which comprises amoxicillin and clavulanic acid, and Tienam, which contains imipenem in combination with cilastatin, a specific inhibitor of the kidney enzyme dihydropeptidase. Clavulanic acid prevents the breakdown of amoxicillin by bacterial enzymes, which allows a therapeutic effect to be achieved with a smaller amount of the preparation as compared to its use without clavulanic acid. Cilastatin slows imipenem metabolism in the kidneys, which leads to utilization of the antimicrobial potential of virtually all the molecules of the antibiotic and to achievement of a therapeutic effect with a smaller amount of imipenem molecules as compared with its use without cilastatin [1].

Implementing selectivity of action of a drug is a complex task due, among other factors, both to the nature of the specific drug-target bond and to the strength of this bond. It has been demonstrated that selectively acting drugs bond weakly with their pharmacological target [1]. This situation means that it is necessary to find a pharmacological target in a specific structural configuration which ensures that reaction centers are accessible to the drug molecules. It has been established that half of protein molecules are inherently polyfunctional [2, 3], which at the structural level is expressed in a specific conformation of the protein molecule adequate to perform a physiologically determined function. Outside of fulfillment of one or another physiological function, the molecule exists in an unstructured state. Various types of chemical modification—phosphorylation, thiolation, glutathionylation, oxidation, etc. —precede the formation of a specific structural conformation and performance of a physiological function. In this connection, the possibility of achieving an effect with one or another drug, and particularly a selectively acting drug, will be determined by finding the target molecule in the appropriate conformation.

There exists a large number of drugs which are potentially useful for the treatment of disease, but which often do not provide the desired effect as a consequence of features of the pharmacodynamics and/or pharmacokinetics. Increasing the dose of a preparation partially solves the problem of achieving a therapeutic effect but is, as a rule, associated with an increase in toxicity. Drugs for the targeted treatment of oncological diseases via an effect-mediating receptor are a typical example.

Thus, the epidermal growth factor receptor (EGFR) is one of the objects which is being studied actively as an anti-tumor target [4, 5, 6].

A number of pharmacological solutions exist which are directed at blocking the biological effect realized via the EGFR:

1) the use of monoclonal antibodies, which bind to the extracellular part of the receptor: Erbitux—monoclonal antibodies to HER1, Herceptin—monoclonal antibodies to HER2/neu; 2) the use of recombinant peptide ligands EGF and/or TGF-a, conjugated with cell-penetrating cytotoxins; 3) the use of low-molecular inhibitors capable of acting on the intracellular domain of EGFR and interrupting the process of tyrosine-kinase phosphorylation of signal-transmitting proteins—Iressa, tyrphostins, genistein, SU6668, ZD6474.

The interaction of antibodies with the immune activity center of a receptor, and of inhibitors with an active center of catalytic activity requires that these centers be accessible, and this in its turn is determined by the conformation of the protein molecule of the receptor. The conformation of the dimeric EGFR molecule makes it possible for tyrosine-kinase inhibitors and monoclonal antibodies to interact with their binding sites. The appropriate conformation of the dimeric EGFR molecule is achieved, among other ways, by oxidative modification, thiolation or glutathionylation of sulfhydryl groups [7].

In this connection, drugs which initiate the process of thiolation or glutathionylation of the EGFR molecule and which initiate formation of the dimeric receptor molecule are capable of increasing the affinity of a drug to the epidermal growth factor receptor when used in combination with drug preparations which interact with the EGFR.

Thus up to the present it has been of interest to create compounds which can interact with the EGFR, enhancing its affinity to drugs.

P-glycoprotein (Pgp) is another target of interest for interaction. Pgp is a trans-membranal protein of the cytoplasmic membrane, is coded for by the MDR1 and MDR2 genes in man, and functions as an ATP-dependent transporter of molecules of various compounds, including molecules of drug preparations, from the cell against the concentration gradient [4]. The functional activity of Pgp is expressed to one extent or another in virtually all mammalian cells of epidermal and mesenchymal origin [4]. P-glycoprotein protects cells against molecules of toxic substances, including drug molecules, removing these from a cell from an intracellular target. The Pgp activity of epithelial cells, which is found only on the apical membrane, prevents molecules of a toxic substance, including drug molecules, entering the body or the tissue of an individual organ. Thus, the entry of molecules of toxic substances, including drug molecules, into the internal environment of the body is restricted thanks to the Pgp activity localized on the apical surface of the intestinal epithelium.

The P-glycoprotein localized on the apical surface of the endothelium of the cerebral vascular plexus restricts entry of harmful substances (including drug molecules) into the brain tissue, functioning as a component of the blood-brain barrier. Low Pgp activity or the absence thereof correlates with increased penetration of molecules of foreign compounds, including drug molecules, into the brain tissue and reduced ability to eliminate toxins into the bile [8]. Pgp activity is regulated at the level of transcription, translation and chemical modification of the protein molecule [9]. MDR1 gene transcription/Pgp activity increases under the influence of growth factors, hormones, anti-tumor preparations, certain antibiotics, ultraviolet irradiation, differentiation-inducing agents, phorbol esters, carcinogens and other chemical, physical and biological agents [4]. The large number of agents initiating Pgp activity act via various signal routes, including signal routes dependent on activation of protein p21 (Ras-protein), phosphatidylinositol-kinase (P13K), and protein-kinase C(PKC) [4]. Inhibitors of Pgp activity, which act on the molecules of the protein, include ion-channel blockers—quinidine, verapamil, nicardipine; antihistamines—terfenadine; antibiotics—cyclosporin, valinomycin, ketoconazole, vinblastine; and hormone antagonists—tamoxifen [1].

The use of inhibitors of Pgp activity in therapeutic practice has found practical application in the treatment of malignant neoplasms for suppressing the drug resistance of tumor cells [1]. Such a limited use of the approach for enhancing the effectiveness of the action of other drugs, the molecules of which are a Pgp substrate, is due to the side-effects of the Pgp inhibitors, which are more dangerous than the positive effect achieved from the action of the drug. Malignant neoplasms are an exception, since resistance of the tumor cells when using cytostatics means that no result is achieved from chemotherapy and that large amounts of cytostatics act on normal cells and have a toxic effect thereon. In this connection the use of Pgp inhibitors is justified, allowing a therapeutic effect to be secured from the chemotherapy drugs and overcoming the drug resistance of the tumor cells due to the Pgp.

New compounds which provide a physiologically adequate suppression of Pgp activity and which would make it possible to avoid the typical toxic effects of known Pgp inhibitors, particularly those such as hemo- and immuno-depression, reduction in the detoxifying function of liver cells, disruption of cardiovascular system function and a number of other effects, are thus also of interest.

In this connection, the object of the present invention was to create compounds capable of enhancing the effectiveness of the action of drug preparations by increasing the affinity of the target to the action of the drug and/or providing therapeutically optimal concentrations of the drug in the microenvironment of the target and/or capable of reducing the toxicity of drugs.

DISCLOSURE OF THE INVENTION

The present invention proposes binuclear coordination compounds of d-metals with aliphatic thiols of general formula I or pharmaceutically acceptable salts thereof (compounds according to the invention), capable of enhancing the effectiveness of the action of biologically active substances forming part of drug preparations:

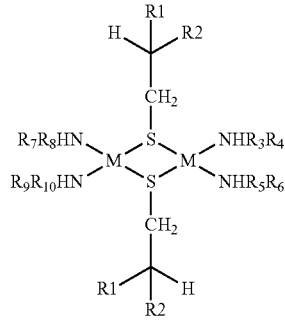

where:

M signifies metal atoms, selected independently from the group comprising: Pd, Fe, Mn, Co, Ni, Cu, Zn and Mo;

$R^1$ and $R^2$, independently of each other, signify a proton (—H), amino (—NH$_2$), hydroxy (—OH), oxo (=O), carboxy (—COOH), cyano (—CN), $C_{1-12}$alkyl (hereinafter designated as R), $C_{2-12}$alkenyl, $C_{2-12}$alkynyl, $C_{1-12}$alkoxy (—OR), $C_{1-12}$alkyl amino (—NH—R), $C_{1-12}$alkoxycarbonyl (—COOR), $C_{1-12}$alkylamido (—CO—NH—R), arylamido, wherein the alkyl groupings included in said substituents may, in their turn, be substituted by one or more than one of the following groups: hydroxy, oxo, carboxy, amino, or amido (—CO—NH$_2$).

$R^3$-$R^{10}$, independently of each other, signify hydrogen, or $NHR^3R^4$ and $NHR^5R^6$, taken together, and/or $NHR^7R^8$ and $NHR^9R^{10}$, taken together, are a ligand containing one or several donor aliphatic or aromatic atoms of nitrogen and occupying the cis-position on the metal atoms (M).

It is desirable that $NHR^3R^4$ and $NHR^5R^6$, taken together, and/or $NHR^7R^8$ and $NHR^9R^{10}$, taken together, are a diamino compound or an aryl with two aromatic nitrogen atoms.

It is desirable that the diamino compound is a $C_2$-$C_6$ diaminoalkylene, and that the aryl contains two pyridyl rings.

It is desirable that $R^3$-$R^{10}$ signify hydrogen, or $NHR^3R^4$ and $NHR^5R^6$, taken together, and/or $NHR^7R^8$ and $NHR^9R^{10}$, taken together, are ethylenediamine, 2,2'-bidipyridyl (2,2'-bipy), 1,10-phenanthroline (1,10-phen), or derivatives thereof.

It is preferable that $R^1R^2CH$—$CH_2$—$SH$ is 2-aminoethanethiol (aet, cysteamine), 2-acetamidoethanethiol, cysteine (Cys), cysteine methyl ester, cysteine ethyl ester, acetylcysteine (Accys), acetylcysteine methyl ester, acetylcysteine ethyl ester, acetylcysteine nitrile, 3-mercaptopropionic acid, γ-glutamine-cysteine-glycine, homocysteine, thioglycolic acid or derivatives thereof.

It is more preferable that $R^3$-$R^{10}$ signify hydrogen, or $NHR^3R^4$ and $NHR^5R^6$, taken together, and/or $NHR^7R^8$ and $NHR^9R^{10}$, taken together, are ethylenediamine, 2,2'-bidipyridyl (2,2'-bipy), 1,10-phenanthroline (1,10-phen), or derivatives thereof, and that $R^1R^2CH$—$CH_2$—$SH$ is 2-aminoethanethiol (aet, cysteamine), 2-acetamidoethanethiol, cysteine (Cys), cysteine methyl ester, cysteine ethyl ester, acetylcysteine (Accys), acetylcysteine methyl ester, acetylcysteine ethyl ester, acetylcysteine nitrile, 3-mercaptopropionic acid, γ-glutamine-cysteine-glycine, homocysteine, thioglycolic acid or derivatives thereof.

A compound according to the invention may have the formula

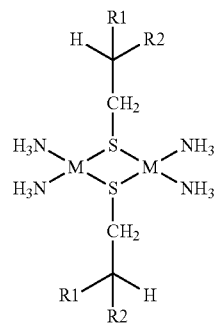

Ia

In a preferred case, a compound according to the invention is selected from the group which comprises [Pd$_2$(μ-S-L-Cys)(μ-S-L-CysH)(2,2'-dipy)$_2$](NO$_3$)$_3$.4.5H$_2$O, Pd$_2$(aetH)$_2$(phen)$_2$](NO$_3$)$_4$.H$_2$O, [Pd$_2$(μ-S-Accys)$_2$(dipy)$_2$]Cl$_2$.H$_2$O, [Pd$_2$(μ-S-Accys)$_2$(NH$_3$)$_4$]Cl$_2$, [Cu$_2$(μ-S-Cys)$_2$(dipy)$_2$]Cl$_2$.

In one of the embodiments, a compound according to the invention is [Pd$_2$(μ-S-L-Cys)(μ-S-L-CysH)(2,2'-dipy)$_2$]-(NO$_3$)$_3$.4.5H$_2$O, which crystallizes in triclinic syngony with spatial group P-1, with elementary cell parameters (A): a=13.86, b=13.82, c=12.17, α=122.13°, β=103.61°, γ=91.40°, V(Å$^3$)=1887.0, Z=1, characterized by an IR spectrum (KBr pellets), v$_{max}$, cm$^{-1}$: 419, 542, 590, 648, 689, 722, 765, 807, 977, 1022, 1036, 1072, 1107, 1164, 1174, 1204, 1226, 1240, 1272, 1312, 1353, 1364, 1384, 1447, 1469, 1563, 1601, 1666, 1728, 3073, 3108, 3221, 3283, 3427, 3953.

In one of the embodiments, a compound according to the invention is Pd$_2$(aetH)$_2$(phen)$_2$](NO$_3$)$_4$—H$_2$O, which crystallizes in monoclinic syngony with spatial group Cc, elementary cell parameters, Å: a=24.53, b=13.10, c=22.65, β=104.26°, V(Å$^3$)=7052.25, Z=4.

In one of the embodiments, a compound according to the invention is [Pd$_2$(μ-S-Accys)$_2$(dipy)$_2$]Cl$_2$.H$_2$O, characterized by an IR spectrum (KBr pellets), v$_{max}$, cm$^{-1}$:507, 640, 692, 774, 815, 879, 946, 1058, 1094, 1212, 1229, 1343, 1381, 1404, 1427, 1573, 1723, 2655, 2820, 2971, 3377, 3406, 3480.

In one of the embodiments, a compound according to the invention is [Pd$_2$(μ-S-Accys)$_2$(NH$_3$)$_4$]Cl$_2$, characterized by an IR spectrum (KBr pellets), v$_{max}$, cm$^{-1}$: 512, 597, 692, 773, 839, 879, 946, 1094, 1212, 1229, 1254, 1343, 1403, 1521, 1572, 1594, 1723, 2655, 2925, 2971, 3119, 3460.

In one of the embodiments, a compound according to the invention is [Cu$_2$(μ-S-Cys)$_2$(dipy)$_2$]Cl$_2$, characterized by an IR spectrum (KBr pellets), v$_{max}$, cm$^{-1}$: 520, 691, 815, 879, 1058, 1133, 1212, 1229, 1254, 1343, 1404, 1572, 1594, 1627, 2655, 2925, 2940, 2971, 3119, 3480.

Compounds according to the invention are characterized in that they make it possible (on condition of their use in small and ultra-small amounts) to accelerate the process of homogeneous selective, "mild" oxidation of the thiol groups of thioaminoacids solely to the formation of disulfide bonds (cross-links) with the assistance of secondary mediators (endogenous active forms of oxygen, nitrogen and other oxidizing agents), which play an important role in the transduction of various signals.

The proposed compounds according to the invention have the ability to act on cell-surface and intracellular receptors and enzymes, the ion channels and transporter proteins of cytoplasmic and intracellular membranes, peptide type extracellular regulatory and transporter molecules, proteins of the cytoskeleton and the extracellular matrix, and other structural, functional and regulatory molecules which include in their composition sulfur residues capable of reversible oxidation-reduction (redox) modification. One of the states of a sulfur residue in a peptide type molecule is the reduced state, in which it is bonded with a proton and comprises a thiol (sulfhydryl) group Pept-SH (Pept is any peptide type molecule). Another of the states of a sulfur residue in a peptide type molecule is the oxidized state. Depending on the nature of the oxidizing agent and the extent of oxidation of the sulfur residue it may be subjected to various chemical oxidative modifications. However, the oxidation variant of physiological importance is that in which the sulfur residue in the cysteine of one polypeptide sequence covalently bonds with the sulfur residue in the cysteine of another polypeptide sequence, forming a disulfide bond—Pept-S—S-Pept. The proposed compounds according to the invention may be used to create medicinal drugs which carry out redox regulation of the physiologically inadequate activity of a target molecule in acute and chronic processes, which in its turn leads to functional concordance of the physiological processes in the cell (Examples 9-14).

The proposed compounds according to the invention have the potential ability to be eliminated from the body in the form of "small clusters" (nano-size particles) after performance of their main catalytic functions and degradation of the initial compound.

The proposed compounds according to the invention may be combined with other biologically active substances added to the composition of drugs (Examples No. 12-14), allowing them to enter the microenvironment of a pharmacological target (Example No. 10) and/or increasing the affinity of a pharmacological target to them (Example No. 9).

Small ($10^{-3}$-$10^{-6}$ mole) and ultra-small (less than $10^{-6}$ to $10^{-15}$ mole) amounts of coordination compounds of d-elements with aliphatic thiols of specific structure may be introduced in order to achieve a biological effect in the mammal body using the enteral, parenteral, inhalation or other route. The action of compounds according to the invention on the molecules of a target in cells restores the functional coherence of cellular processes, and the ability of cells to respond appropriately to biologically active substances, both intrinsic, i.e. synthesized in the body, and also introduced from outside the body in physiologically optimal doses, which makes it possible to avoid high concentrations of biologically active substances introduced as part of drug preparations in order to achieve the therapeutic objectives.

The action of compounds according to the invention on cells leads to elevation of the concentration of biologically active substances introduced as part of a drug into the microenvironment of an intracellular pharmacological target due, among other reasons, to a reduction in the activity of proteins responsible for multiple drug resistance (Example No. 10). A particular feature of the biological activity of the structures of the binuclear coordination compounds of d-elements with aliphatic thiols now proposed is the ability to induce only the synthesis of enzymes of the second phase of detoxification of xenobiotics, which have little effect on inactivation of most of the biologically active substances introduced as part of drug preparations, but which increase the resistance of cells to negative environmental factors, increase in the level of which is due to the illness and/or the action of the drug (Example 11).

Compounds according to the invention are thus promising chemical molecules for creating drug preparations for external, inhalation, enteral and parenteral use, used both in combination with chemical molecules having a known biological effect and pharmacological activity, used in drugs for etiotropic, pathogenetic and symptomatic therapy, and also with newly synthesized chemical molecules having a biological activity required in pharmacological solutions. Compounds according to the invention facilitate manifestation of the pharmacological activity of biologically active chemical molecules in physiologically optimal doses.

In particular, the proposed compounds according to the invention may act on the EGFR, increasing its affinity to pharmacologically active molecules (Example No. 9). Compounds according to the invention which comply with general formula I shown above are also capable of increasing the concentration a drug in cells by inhibiting P-glycoprotein (Example No. 11).

The proposed compounds according to the invention can also be represented by formula II

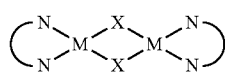

where M signifies the metal atoms described above, X are residues of aliphatic thiols or derivatives thereof, which perform a bridging function (μ-X) via a sulfur atom, N are donor nitrogen atoms of bidentate nitrogen-containing ligands (L), which may be substituted by two bidentate-coordinated molecules of ethylenediamine or four monodentate-coordinated terminal molecules of ammonia.

A bridge according to the invention may be designated by the formula (M-(μ-SCH$_2$CHR$^1$R$^2$)-M).

Aliphatic thiols according to the invention may be designated by the formula R$^1$R$^2$CH—CH$_2$—SH, where the sulfur atom is bonded to an sp$^a$-hybridized carbon atom, while R$^1$ and R$^2$, independently of each other, signify a proton (—H), amino (—NH$_2$), hydroxy (—OH), oxo (═O), carboxy (—COOH), cyano (—CN), C$_{1-12}$alkyl, C$_{2-12}$alkenyl, C$_{2-12}$alkynyl, C$_{1-12}$alkoxy (—OR), C$_{1-12}$alkylamino (—NH—R), C$_{1-12}$alkoxycarbonyl (—COOR), C$_{1-12}$alkylamido (—CO—NH—R), arylamido, wherein the alkyl groupings included in said substituents may, in their turn, be substituted by one or more than one of the following groups: hydroxy, oxo, carboxy, amino, or amido (—CO—NH$_2$) where R designates a C$_{1-12}$ alkyl residue.

In specific embodiments, X may be

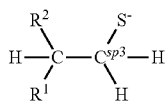

In these cases, the thiols indicated are 2-aminoethanethiol (aet, cysteamine) (1), 2-acetamido-ethanethiol (2), cysteine (Cys) (3), cysteine methyl ester (4), cysteine ethyl ester (5), acetylcysteine (Accys) (6), acetylcysteine methyl ester (7), acetylcysteine ethyl ester (8), acetylcysteine nitrile (9), 3-mercaptopropionic acid (10), γ-glutamine-cysteine-glycine (11), homocysteine (12), thioglycolic acid (13).

If not otherwise indicated, the following terms, used in the set of claims presented below and in the specification, have the definitions given below.

The indication that "NHR$^3$R$^4$ and NHR$^5$R$^6$, taken together, and/or NHR$^7$R$^8$ and NHR$^9$R$^{10}$, taken together, are a ligand containing one or several donor aliphatic or aromatic atoms of nitrogen and occupying the cis-position on the metal atoms (M)" means that R$^3$-R$^6$, together with the nitrogen atoms to which they are connected, form a ligand containing one or several donor aliphatic or aromatic atoms of nitrogen, the ligands occupying the cis-position on the metal atoms (M), for example a diamino-compound or an aryl (heteroaryl), and/or R$^7$-R$^{10}$, together with the nitrogen atoms to which they are connected, form a ligand containing one or several donor aliphatic or aromatic atoms of nitrogen, the ligands occupying the cis-position on the metal atoms (M), for example a diamino-compound or an aryl (heteroaryl).

The term "cis-positioned ligands" corresponds to coordination compounds in which the stipulated ligands occupy adjacent positions in the square-planar configuration of the coordination compound, while "trans-disposed ligands" corresponds to the disposition of ligands opposite one another on the metal atom.

The term "alkyl" for substituents R$^1$ and R$^2$ in said claims signifies a linear or branched saturated hydrocarbon residue with from 1 to 12, preferably from 1 to 6, for example from 1 to 4, carbon atoms, such as methyl, ethyl, n-propyl, iso-propyl, iso-butyl, tert-butyl, etc.

Said term "alkyl" for substituents R$^1$ and R$^2$ in said formula R$^1$R$^2$CH—CH$_2$—SH may also be understood as a linear or branched saturated hydrocarbon residue, containing a double or triple bond, but linked to a carbon of the general formula R$^1$R$^2$CH—CH$_2$—SH via an sp$^3$ hybridized carbon atom (—CH$_2$—CH═CH$_2$) or propargyl (—CH$_2$-C≡CH).

The term "alkenyl" signifies linear or branched unsaturated hydrocarbon residues with 2-12 carbon atoms and containing a double bond, the bond of the substituents R$^1$ and R$^2$ in the structure R$^1$R$^2$CH—CH$_2$—SH being made via an sp$^2$ hybridized carbon atom. R$^1$ and R$^2$ preferably contain from 2 to 4 carbon atoms. Ethenyl (vinyl (—CH═CH$_2$)) or propenyl (—CH═CH—CH$_3$) are examples.

The term "alkynyl" signifies linear or branched unsaturated hydrocarbon residues with 2-12 carbon atoms, containing a triple bond, the bond of the substituents R$^1$ and R$^2$ in the structure R$^1$R$^2$CH—CH$_2$—SH being made via an sp hybridized carbon atom. R$^1$ and R$^2$ preferably contain from 2 to 4 carbon atoms. Propynyl (—C≡C—CH$_3$) is an example.

The term "alkoxy" signifies an alkyl residue in the sense of the definition given above, bonded via an oxygen atom. Alkoxy may be represented by the formula R—O—, where R signifies an alkyl residue. Examples of "alkoxy" residues include methoxy (—OCH$_3$), ethoxy (—OC$_2$H$_5$), isopropoxy (—O-(i-Pr)), etc.

The term "alkylamino" signifies a group with the formula —NH—R.

The term "alkoxycarbonyl" signifies a group with the formula —COOR, such as carboxyethyl (—COOC$_2$H$_5$) or carboxymethyl (—COOCH$_3$).

The term "alkylamido" signifies a group with the formula —CO—NH—R.

In the definitions given above, R signifies alkyl in the sense in which it is defined above.

The term "aryl" signifies an aromatic radical containing from 3 to 7 carbon atoms, such as phenyl, naphthyl or imidazolyl. An aryl may also contain hetero-atoms, for example hetero-atoms of nitrogen, oxygen and sulfur (heteroaryl). In particular, an aryl in the definition of $R^1$ and $R^2$ signifies an aromatic radical containing from 3 to 7 carbon atoms and possibly including hetero-atoms. An aryl forming part of a ligand, containing one or several donor aliphatic or aromatic nitrogen atoms, on the metal atoms (M) may be a monocyclic aryl or a polycyclic aryl (heteroaryl) and the rings may be condensed or joined by a bridging bond. In this case the aryl may be phenanthroline, pyridine or dipyridyl.

The term "diamino-compound" signifies an aliphatic group with two amino groups (—$NH_2$), for example a $C_2$-$C_{10}$ or preferably a $C_{2-6}$ aliphatic or alkylene group with two amino groups. In particular, "$C_2$-$C_6$ diaminoalkylene" signifies a [(—$CH_2$)$_{2-6}$]alkylene with two amino groups, such as ethylenediamine ($H_2N(CH_2)_2NH_2$).

A ligand or ligands containing aliphatic or aromatic donor atoms of nitrogen and occupying the cis-position on the M atoms in a coordination compound may, for example, be cyclic molecules of ethylenediamine ($H_2N(CH_2)_2NH_2$), 1,10-phenanthroline (1,10-phen), 2,2'-dipyridyl (2,2'-dipy) or derivatives thereof, and also monodentate-coordinated molecules of ammonia or pyridine.

In the event that a ligand L has only one aliphatic or aromatic nitrogen atom free to coordinate to a metal atom, the framework of the coordination compound may be described by the empirical formula $L_2M(\mu\text{-}X)_2ML_2$ and may be represented by graphic formula IIa:

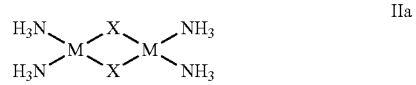

IIa

The main function of the aliphatic or aromatic amines occupying cis positions on a d-metal atom is the possibility of forming binuclear compounds with two bridging thiolate ligands. It is precisely the presence of two bridging ligands in such a binuclear coordination compound which makes it possible to perform a synchronous two-electron process of oxidation of the thiolates by endogenous oxidizing agents (active forms of oxygen) which are present in the body.

The presence of aliphatic or aromatic amines occupying cis positions on the d-metal atom is responsible for the high biological activity of the coordination compounds. This feature of the structural organization of the coordination compounds determines their biological activity as the basic property of biological targets to interact with specific isomers of drug molecules, which act on the biological molecules and determine the therapeutic action of the drug. Other isomers of the same chemical molecule either have little activity or are inert in relation to the biomolecules and possess no therapeutic activity.

It is precisely the structural organization of molecules of coordination compounds, and not the generality of their chemical composition, which determines their biological activity.

A ligand or ligands, coordinated in cis-positions on a metal atom, make it possible to obtain binuclear compounds containing two bridging thiolate groups.

The proposed compounds may also be in the form of salts.

The term "pharmaceutically acceptable salt" relates to any salt prepared with an inorganic or organic acid or base, which salt can be used safely in the treatment of persons or animals.

Pharmaceutically acceptable salts can easily be prepared using methods known from the prior art, taking account of the chemical properties of the compound which is to be converted into a salt. Inorganic or organic acids such as, for example, hydrochloric, hydrobromic, sulfuric, nitric, phosphoric, citric, formic, fumaric, maleic, acetic, succinic, tartaric, methanesulfonic, p-toluenesulfonic acid, etc., are suitable for the formation of pharmaceutically acceptable salts of a basic compound of formula I, II or IIa.

Compounds according to the invention may be prepared using the schemes shown below, which are comprehensible to specialists.

General Schemes for the Preparation of Coordination Compounds of d-Elements with Aliphatic Thiols I, II or IIa

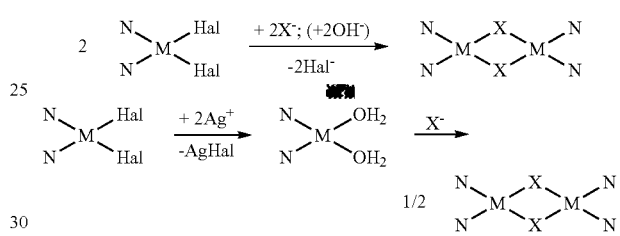

where Hal signifies a halogen atom (preferably Cl, Br or I), M signifies the metal atoms described above (the metals in the composition of the coordination compounds may be different), X are residues of aliphatic thiols or derivatives thereof, described above, which perform a bridging function, and N are donor atoms, of nitrogen-containing ligands (L).

A compound according to the invention may be prepared by a method which will be clear to a specialist, proceeding from the proposed structure of a coordination compound and the methods shown in the general schemes.

A coordination compound according to the invention may be prepared by taking an aqueous solution or suspension of a compound of a cis-halide coordination compound of a d-metal and adding thereto a ligand (an aliphatic thiol) in the dry form, or in the form of a solution or suspension. The formation of binuclear coordination compounds containing bridging thiolate ligands occurs in the resultant system.

The degree of dilution for each particular compound may be chosen empirically. An accurate judgment as to the formation of binuclear coordination compounds may be made on the basis of physico-chemical studies (particularly X-ray structural studies) and the results of advanced quantum-chemical calculations confirming that they function as oxidation catalysts [11, 12]. In vitro catalysis by said compound of an oxidation-reduction reaction, where the sulfur of the thiolate groups is oxidized with the formation solely of disulfide bonds, can serve as an indirect criterion of the presence of such a structure.

The ionization energy (IE) of the thiolate ligands —$SCH_2C(H)R^1R^2$ can be used as a characteristic of their donor capacity, i.e. the ability to form complexes with ions of d-elements: the lower the IE values, the higher the anticipated donor properties of the ligand. IE values of —$SCH_2C(H)R^1R^2$ anions calculated as examples are presented in Table 1.

TABLE 1

Results of quantum-chemical DFT calculations of ionization
energy (IE, eV) of thiolate anions and charges
on sulfur atoms q(S) (CC-PVTZ(-F) + basis)

| Compound | IE(RS$^-$) | q(S) |
|---|---|---|
| $CH_3S^-$ | 1.90 | −0.84 |
| $C_2H_5S^-$ | 1.97 | −0.74 |
| $C_3H_7S^-$ | 1.97 | −0.78 |
| $C_4H_9S^-$ | 1.98 | −0.72 |
| $NH_2C_2H_4S^-$ | 2.06 | −0.71 |
| $NH_2CHCOOHCH_2S^-$ | 2.51 | −0.67 |

Calculations of the electron structure of compounds were performed by the DFT B3LYP(CC-PVTZ(−F)+basis) method using the Jaguar 7.5 software package.

The same table gives the calculated charges on the sulfur atom which is the complex-forming atom of the catalytic cycle of thiol oxidation. An increase in the electron density on the sulfur atom, i.e. growth of the negative charge, facilitates the formation of strong bonds with the metal ion. Thus, in the series of thiolate anions SW now considered, their donor capacities should rise in the series:

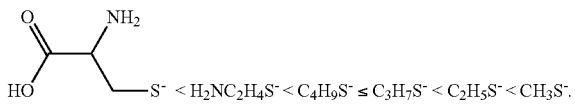

It should also be noted that the information obtained from the results of quantum-chemical calculations can also facilitate identification of a correlation between the geometric structure of compounds and the physiological activity of the drug preparations obtained.

A typical catalytic cycle of oxidation of aliphatic thiols in the presence of coordination compounds is as follows:

Pharmaceutically acceptable forms of a preparation may be prepared in accordance with methods known from the prior art with allowance for the chemical properties of the coordination compound, the aliphatic thiol or a derivative thereof and the pharmaceutically active compound. It is preferable that the molar ratio of the coordination compound to the molecule of aliphatic thiol in a preparation should be from 1:50 to 1:50000. The aliphatic thiol:pharmaceutically active compound ratio is selected empirically.

A preparation may be a therapeutic form which is convenient in use (solid, liquid, soft, inhalation, etc.) and which allows the required therapeutic effect to be achieved.

An excess of thiol ensures that it is possible to prepare and use small and ultra-small doses of coordination compounds of d-metals as part of a preparation.

Compounds according to the invention are used in the form of pharmaceutical preparations (therapeutic forms) for pharmacotherapy. The terms pharmacotherapy and pharmacotherapeutic action are employed in the invention in the generally accepted sense of treatment with drugs. Pharmaceutical preparations of compounds according to the invention may be administered perorally, i.e. as therapeutic forms such as solutions, emulsions or suspensions, and also tablets, coated tablets, pills, and hard and soft gelatin capsules. Rectal administration may also be effective, i.e. as therapeutic forms such as suppositories. Parenteral administration is effective, in the form of solutions for subcutaneous, intramuscular, intravascular and intracavitary injections, and for inhalations. A compound according to the invention may also be used externally (ointments, creams, etc.) or be administered by inhalation, intranasally and/or perorally by any other method ensuring delivery of the pharmaceutical preparation into the patient's body.

In order to obtain pharmaceutical preparations (therapeutic forms), compounds according to the invention are combined in a unified therapeutic form with therapeutically inert inorganic or organic vehicles. Lactose, maize starch or derivatives

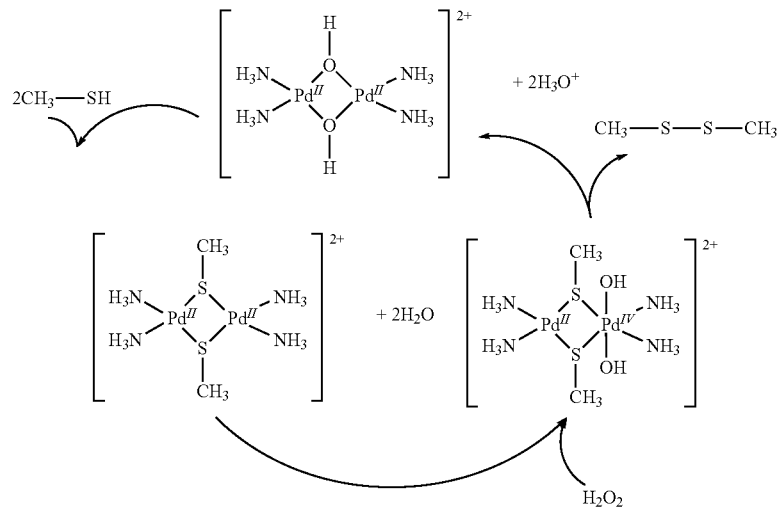

A compound according to the invention may form part of a preparation which includes a coordination compound and free molecules of an aliphatic thiol (or derivatives thereof) not bonded to the coordination compound. The coordination compound and free molecules of an aliphatic thiol (or derivatives thereof) in a preparation may be in the cationic or the anionic form, or in the form of neutral particles.

thereof, talc, stearic acid or salts thereof, etc. may, for example, be used as such vehicles for tablets, coated tablets, pills and hard gelatin capsules. Vegetable oils, waxes, fats, semi-solid and liquid polyols, etc. are, for example, suitable vehicles for soft gelatin capsules. Water, polyols, sucrose, invert sugar, glucose, etc. are, for example, suitable vehicles for preparing solutions and syrups. Natural or hydrogenated oils, waxes, fats, semi-liquid or liquid polyols, etc. are suitable vehicles for suppositories.

Furthermore, pharmaceutical preparations may contain preservatives, solubilizers, stabilizers, wetting agents, emulsifiers, sweetening agents, colorants, correctives, salts to regulate osmotic pressure, buffers, masking agents or antioxidants and other components needed for preparation of the therapeutic form.

The auxiliary substances indicated above, which are used to create therapeutic forms, will henceforward be referred to as "therapeutically inert excipients". However, therapeutic forms of a compound according to the invention may also contain free molecules of aliphatic thiols and/or other therapeutically active substances.

A compound according to the invention may form part of a preparation which includes a coordination compound and free molecules of an aliphatic thiol (or derivatives thereof) which are not bonded to the coordination compound. The coordination compound and free molecules of aliphatic thiol (or derivatives thereof) in a preparation may be in either the cationic or the anionic form, or in the form of neutral particles.

Pharmaceutically acceptable forms of a preparation may be prepared in accordance with methods known from the prior art with allowance for the chemical properties of the coordination compound and the aliphatic thiol (or a derivative thereof). It is preferable that the molar ratio of the atom of d-metal of the coordination compound to the molecule of aliphatic thiol in the preparation should be from 1:50 to 1:50000.

A preparation may be a therapeutic form which is convenient in use (solid, liquid, soft, inhalation, etc.) and which allows the required therapeutic effect to be achieved.

An excess of thiol ensures that it is possible to prepare and use small and ultra-small doses of coordination compounds of d-metals as part of a preparation. Such a preparation ensures more precise dosing, which is important when a compound according to the invention is administered in small and ultra-small amounts.

According to the invention, the proposed means may be utilized to enhance the therapeutic activity of a particular pharmacologically active substance.

In the context of this specification, increasing the therapeutic effectiveness of a pharmacologically active substance comprises reducing the single or course dose as a consequence of raising the affinity of the target to the drug and/or increasing the concentration of the drug in the area of the pharmacological target and, as a consequence, reducing the general toxicity for the customary therapeutic dose of this pharmacologically active substance.

A pharmacologically active substance is to be understood as any substance which is used for pharmacotherapeutic purposes.

When a compound according to the invention is used to enhance the pharmacotherapeutic effectiveness of a particular pharmacologically active substance, this pharmacologically active substance may be introduced into the inner region of a coordination compound according to the invention as a ligand. It may also be located in the outer region (as a counter-ion, for example). A pharmacologically active substance may also be present in excess relative to the means according to the invention in a pharmaceutically acceptable therapeutic form.

Pharmaceutically acceptable forms of a preparation may be prepared in accordance with methods known from the prior art with allowance for the chemical properties of the coordination compound and the pharmaceutically active compound. The aliphatic thiol:pharmaceutically active compound ratio is selected empirically.

Therapeutic forms (solid, liquid, soft, inhalation, etc.) can easily be prepared in accordance with methods known from the prior art with allowance for the nature of the pharmacologically active substance, which is used in excess relative to the compound according to the invention.

In the cases enumerated, a compound according to the invention and pharmacologically active substances, the effectiveness of which they enhance, are contained in a single therapeutic form. This case naturally ensures that they are administered simultaneously.

A compound according to the invention and a pharmacologically active substance, the effectiveness of which is to be enhanced with the aid thereof, may be contained in separate therapeutic forms.

Administration in separate therapeutic forms may be carried out simultaneously (taking two solid dosed therapeutic forms, such as tablets, simultaneously, simultaneous injection, particularly in a single syringe), or sequentially, when initially a first therapeutic form and then a second therapeutic form are given or administered to a patient. The interval between the administration is preferably not more than 1 hour, but may be increased while a synergetic effect is still observed.

It must be noted that the ligand in the coordination compound now proposed is a physiologically (biologically, pharmacologically) and pharmaceutically acceptable compound.

A physiologically (biologically, pharmacologically) acceptable compound is to be understood as a compound which does not cause toxic or otherwise undesirable effects when administered to a patient. The terms physiologically acceptable, biologically acceptable and pharmacologically acceptable are to be considered as synonyms in the context of this specification. It is also to be understood that all the substances used are also pharmaceutically acceptable, i.e. they may be used as ingredients in therapeutic forms.

In the context of this invention, patient signifies a human or other mammal, birds, amphibians or fish, to which a therapeutic form is to be administered by one method or another.

The ligand and d-metal may also possess intrinsic pharmacological activity.

The amount of the coordination compound of aliphatic thiols with d-metals administered, referred to the biometals, is determined by the proportion by weight of the biometal in the composition of the coordination compound, and may correspond to or be less than the daily requirements for the biometal employed; otherwise the amount of the d-metal administered as part of the coordination compound is determined by the need to achieve a treatment result. The amount of the coordination compound of d-metals administered, not referred to biometals, is determined by the proportion by weight of d-metal in the composition of the coordination compound and must be less than the maximum permissible values thereof; otherwise the amount of the d-metal administered as part of the coordination compound is determined by the need to achieve a treatment result.

In one of the embodiments, the invention relates to a method for treatment of a mammal (a human, for example) suffering from an oncological disease (cancer), in which an effective amount of a coordination compound (complex), here disclosed, and an effective amount of an EGFR inhibitor (Iressa, tyrphostins, genistein, SU6668, ZD6474) are administered to a mammal. Examples of oncological diseases which can be treated by this method include cancer of the lungs, breast, head and neck, gastro-intestinal tract, ovaries, kidneys, skin, nervous system, brain and connective tissue.

In one of the embodiments, the invention relates to a method for treatment of a mammal (a human, for example) suffering from metabolic syndrome, type one or two diabetes mellitus, diabetic retinopathy in patients with type two diabetes mellitus, diabetic foot syndrome in patients with type two diabetes mellitus, trophic ulcers of the lower extremities in patients with type two diabetes mellitus, or diabetic neuropathy in patients with type two diabetes mellitus, in which an effective amount of a coordination compound (complex) here disclosed and an effective amount of thioctic acid are administered to the mammal.

In one of the embodiments, the invention relates to a method for the prophylaxis or treatment of cardio-vascular disease, in which an effective amount of a coordination compound (complex), here disclosed, and an effective amount of adenosine are administered to a mammal. Acute and chronic ischemic heart disease, myocardial infarct and stenocardia are, in particular, examples of cardio-vascular diseases.

In one of the embodiments, the invention relates to a method for the treatment of post-irradiation hemodepression, toxic hemodepression and post-traumatic hemodepression, mental disorders of manic-depressive or melancholic psychosis type, and arthritis of varying origin, in which an effective amount of a coordination compound (complex), here disclosed, and an effective amount of lithium are administered to a mammal.

EXAMPLES

The invention will now be explained by specific examples.

Example No. 1

Preparation of a coordination compound of Pd(II) with cysteine (in aqueous solution is the cation $[Pd_2(\mu\text{-S-L-Cys})(\mu\text{-S-L-CysH})(2,2'\text{-dipy})_2]^{3+}$)

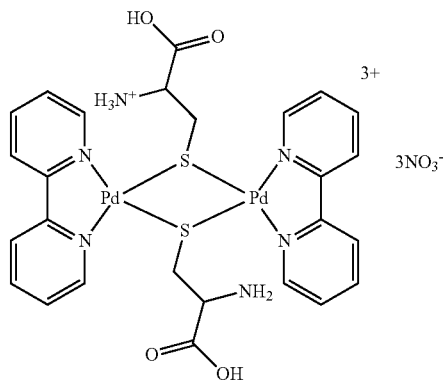

221 mg (1.811 mmole) of $AgNO_3$, dissolved in the minimum amount of water, are added to a suspension of 300 mg (0.904 mmole) of $Pd(2,2'\text{-dipy})Cl_2$ in 15 ml of water. The mixture is acidified with 0.5 ml of concentrated $HNO_3$, homogenized in an ultrasound bath for 15 min and filtered. 96 mg (0.905 mmole) of L-cysteine (cys), dissolved in the minimum amount of water, are added to the filtrate. The reaction mixture is evaporated in air at room temperature. The dark orange crystals of $[Pd_2(\mu\text{-S-L-Cys})(\mu\text{-S-L-CysH})(2,2''\text{-dipy})_2](NO_3)_3 \cdot 4.5H_2O$ which precipitate are readily soluble in water, less soluble in ethanol, and virtually insoluble in acetone and dichloromethane. Yield 70-75%.

Elementary analysis: found, %: C, 21.85; N, 11.13; Pd, 24.02; S, 7.23.

Calculated for $C_{16}H_{32}N_7O_{17.5}Pd_2S_2$ ($[Pd_2(\mu\text{-cys})(\mu\text{-cysH})(dipy)_2]\text{-}(NO_3)_3 \cdot 4.5H_2O$, MW 1034.1 g/mol), %: C, 21.87; N, 11.17; Pd, 24.13; S, 7.28.

Crystallizes in triclinic syngony with spatial group P-1, parameters of elementary cell, Å: a=13.86, b=13.82, c=12.17, α=122.13°, β=103.61°, γ=91.40°, V(Å³)=1887.0, Z=1, R=7.02%.

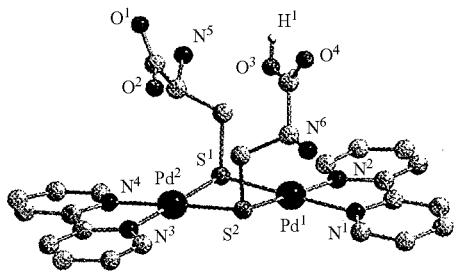

In the solid state, $[Pd_2(\mu\text{-cys})(\mu\text{-cysH})(dipy)_2](NO_3)_3$ molecules bond in pairs via palladium atoms due to weak non-covalent interactions.

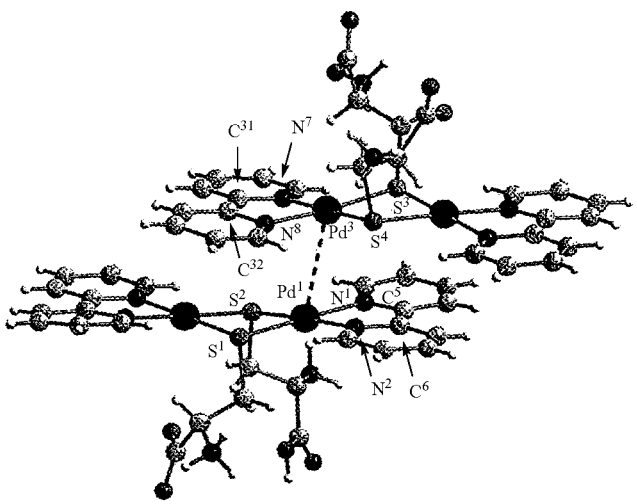

In general, "structuring" of the molecules of the complex compound occurs due to Pd—Pd interactions between metal ions, the system of hydrogen bonds and inter-ligand π-π interactions which leads to the formation of "chains" within the crystal structure.

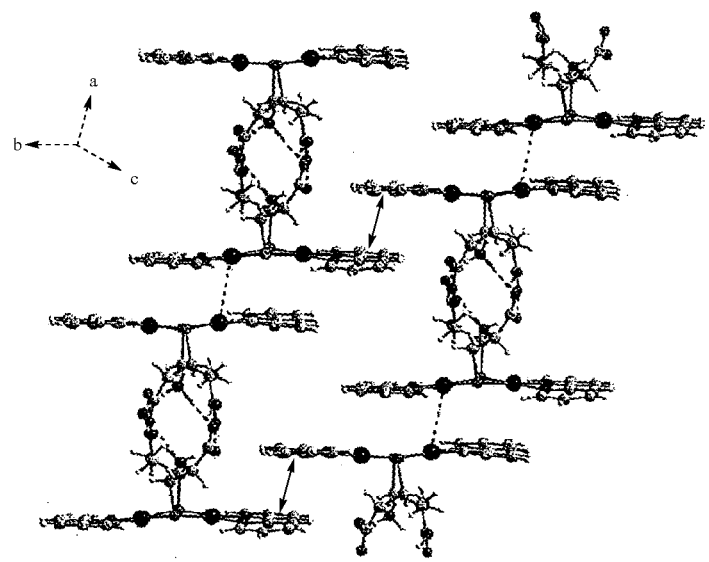

Formation of 1D chains directed along [100], and 2D layers in the (010) plane. Arrows indicate π-π stacking interactions between dipyridyl fragments of adjacent 1D chains.

The coordinates and thermal parameters of the atoms have been deposited in the Cambridge Structural Database (CCDC) under number 705745.

IR spectrum (KBr pellets), $v_{max}$, cm$^{-1}$; 419, 542, 590, 648, 689, 722, 765, 807, 977, 1022, 1036, 1072, 1107, 1164, 1174, 1204, 1226, 1240, 1272, 1312, 1353, 1364, 1384, 1447, 1469, 1563, 1601, 1666, 1728, 3073, 3108, 3221, 3283, 3427, 3953.

The coordination compound was added to an excess of ligand, for which purpose 0.1 g of the complex [Pd$_2$(μ-S-L-Cys)(μ-S-L-CysH)(2,2'-dipy)$_2$](NO$_3$)$_3$.4.5H$_2$O was added to a solution containing 9.97 g of L-cysteine dissolved in 100 ml of water; this was thoroughly stirred and the resultant solution was dried by sublimation under vacuum, resulting in the formation of a light yellow substance in which the coordination compound/organic molecule ratio was 1/1000.

The substance was ready for use on completion of vacuum-sublimation drying.

Example No. 2

Preparation of a coordination compound of Pd(II) with cysteamine.

In aqueous solution, the coordination compound is the cation [Pd$_2$(μ-SCH$_2$CH$_2$NH$_3$)$_2$(1,10-phen)$_2$]$^{4+}$.

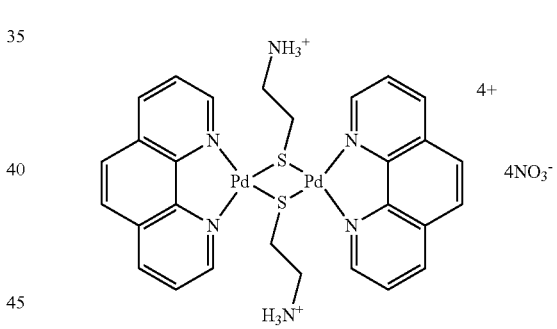

A solution containing 0.509 g (2.99 mmole) of silver nitrate (in the minimum amount of water) was added to a suspension of 571 mg (1.49 mmole) of Pd(1,10-phen)Cl$_2$ in 20 ml of water which had been acidified to pH 3 with 1M nitric acid. The resultant curd-like precipitate of silver chloride was coagulated by careful heating on a water bath and was centrifuged off. After separating off the precipitate, 170 mg of 2-aminoethanethiol (aet, cysteamine) hydrochloride was dissolved in the centrifugate. Lamellar orange-red crystals were deposited during slow evaporation of the orange solution in air during several weeks. Yield 0.25 g (35%).

Elementary analysis: found. %: C, 33.5; N, 14.0; Pd, 21.2; S, 6.60.

Calculated for C$_{28}$H$_{32}$N$_{10}$O$_{13}$Pd$_2$S$_2$ ([Pd$_2$(aetH)$_2$(phen)$_2$]-(NO$_3$)$_4$.H$_2$O, MW 993.59 g/mol), %: C, 33.85; N, 14.10; Pd, 21.42; S, 6.45.

[Pd$_2$(μ-S-CystH)$_2$(1,10-phen)$_2$](NO$_3$)$_4$.H$_2$O crystallizes in monoclinic syngony with spatial group Cc, elementary cell parameters, Å: a=24.53, b=13.10, c=22.65, β=104.26°, V(Å$^3$)=7052.25, Z=4, R=3.16%

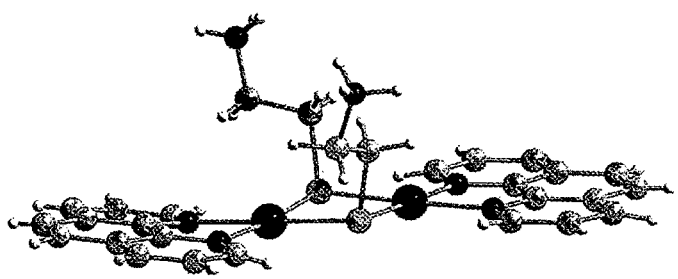

In order to obtain a preparation, the coordination compound was transferred into an excess of ligand, for which purpose 0.1 g of the complex [Pd$_2$(μ-SCH$_2$CH$_2$NH$_3$)$_2$(1,10-phen)$_2$](NO$_3$)$_4$·H$_2$O was added to a solution containing 11.43 g of cysteamine (aminoethanethiol) hydrochloride dissolved in 100 ml of water; this was thoroughly stirred and the resultant reaction solution was dried by sublimation under vacuum, resulting in the formation of a light-yellow substance in which the coordination compound/organic molecule ratio was 1/1000.

The substance was ready for use on completion of vacuum-sublimation drying.

Example No. 3

Preparation of a coordination compound of Pd(II) with acetylcysteine

In aqueous solution, the coordination compound is the cation [Pd$_2$(μ-S-Accys)$_2$(dipy)$_2$]$^{2+}$

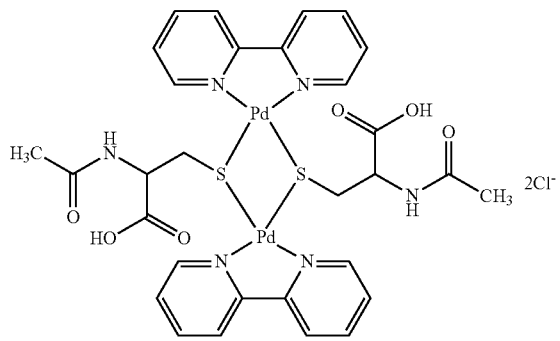

77.8 mg of acetylcysteine (0.476 mmole) were added with stirring to a suspension of 0.160 g of Pd(2,2'-dipy)Cl$_2$ (0.476 mmole) in 10 ml of water, and 0.5 M KOH solution was added to pH 11. The solution was held for one hour in a water bath at 50° C. ~70 ml of acetone were added to the resultant solution, which was stirred, and then ~80 ml of diethyl ether were additionally added. Yellow acicular crystals of the complex [Pd$_2$(μ-S-Accys)$_2$(dipy)$_2$]Cl$_2$·H$_2$O were precipitated when the reaction mixture was left to stand for several hours.

Elementary analysis: found, %: C, 38.6; N, 9.0; Pd, 22.29; S, 6.65.

Calculated for C$_{30}$H$_{34}$Cl$_2$N$_6$O$_7$Pd$_2$S$_2$ [Pd$_2$(μ-S-Accys)$_2$(dipy)$_2$]·Cl$_2$·H$_2$O, MW 938.5 g/mol, %: C, 38.39; N, 8.95; Pd, 22.68; S, 6.83.

IR spectrum (KBr pellets), ν$_{max}$, cm$^{-1}$: 507, 640, 692, 774, 815, 879, 946, 1058, 1094, 1212, 1229, 1343, 1381, 1404, 1427, 1573, 1723, 2655, 2820, 2971, 3377, 3406, 3480.

In order to obtain a preparation, the coordination compound was transferred into an excess of ligand, for which purpose 0.1 g of the complex [Pd$_2$(μ-S-Accys)$_2$(dipy)$_2$]Cl$_2$·H$_2$O was added to a solution containing 17.39 g of acetylcysteine dissolved in 1000 ml of water, this was thoroughly stirred and the resultant solution was dried by sublimation under vacuum, resulting in the formation of a light yellow substance in which the coordination compound/organic molecule ratio was 1/1000.

The substance was ready for use on completion of vacuum-sublimation drying.

Example No. 4

Obtaining a preparation comprising lithium ions, acetylcysteine and a binuclear coordination compound of palladium with acetylcysteine.

In aqueous solution, the coordination compound is the cation [Pd$_2$(μ-S-Accys)$_2$(NH$_3$)$_4$]$^{2+}$

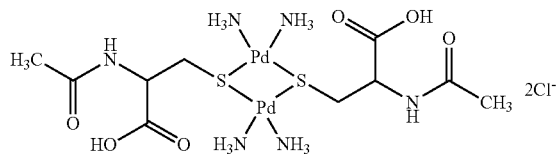

0.386 g of acetylcysteine (2.36 mmole) was added cold to a suspension of cis-[Pd(NH$_3$)$_2$Cl$_2$] (0.5 g, 2.36 mmole), and 0.5 M KOH solution was added to pH 11. The solution was held in a water bath at 50° C. for one hour. ~50 ml of acetone were added to the resultant solution, which was stirred, and then ~50 ml of diethyl ether were additionally added. The light yellow deposit of the complex [Pd$_2$(μ-S-Accys)$_2$(NH$_3$)$_4$] Cl$_2$ which precipitated was filtered off and dried in a vacuum desiccator.

Elementary analysis: found %: C, 17.6; N, 12.2; Pd, 30.0; S, 10.0.

Calculated for C$_{10}$H$_{28}$Cl$_2$N$_6$O$_6$Pd$_2$S$_2$ [Pd$_2$(μ-S-Accys)$_2$(NH$_3$)$_4$]Cl$_2$, MW 676.24 g/mol, %: C, 17.76; N, 12.43; Pd, 31.47; S, 9.48.

IR spectrum (KBr pellets), ν$_{max}$, cm$^{-1}$: 512, 597, 692, 773, 839, 879, 946, 1094, 1212, 1229, 1254, 1343, 1403, 1521, 1572, 1594, 1723, 2655, 2925, 2971, 3119, 3460.

g of the complex [Pd$_2$(μ-S-Accys)$_2$(NH$_3$)$_4$]Cl$_2$ was added to 150 ml of a solution containing 24.13 g of anhydrous acetylcysteine and stirred, and 6.2 g of lithium hydroxide monohydrate LiOH·H$_2$O were added in small portions, stirring until completely dissolved. The resultant solution was titrated to pH 7.2-7.4 with saturated aqueous solution of lithium hydroxide, The preparation can be synthesized without a stage of isolation of the coordination compound in the solid phase. In this case, a weighed amount of cis-[Pd(NH$_3$)$_2$Cl$_2$] is added to an aqueous solution of the calculated amount of acetylcysteine and the solution is stirred until fully dissolved, after which the calculated amount of anhydrous lithium hydroxide or lithium hydroxide monohydrate is added. After fully dissolving, the solution is titrated to pH 7.0-7.4 with saturated lithium hydroxide solution.

The substance is ready for use after sublimation drying under vacuum.

Example No. 5

Preparation of a coordination compound of copper with cysteine.

In aqueous solution, the coordination compound is the cation [(2,2'-dipy)Cu(μ-Cys)$_2$Cu(2,2'-dipy)]$^{2+}$

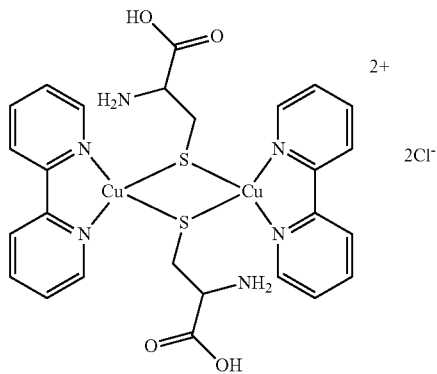

An ethanol solution of cysteine (0.94 g, 7.7 mmole) is added to an ethanol solution of Cu(2,2'-dipy)Cl$_2$ (1 g, 3.44 mmole, Cu:Cys molar ratio 1:2.25). The reaction mixture is heated for several minutes, then a finely crystalline deposit of the complex is precipitated when the mixture is slowly cooled and this is separated from the solution by filtering, washed with diethyl ether and dried in a vacuum desiccator.

Elementary analysis: found %: C, 41.5; N, 11.0; Cu, 16.5; S, 8.3.

Calculated for C$_{26}$H$_{28}$Cl$_2$Cu$_2$N$_6$O$_4$S$_2$ [Cu$_2$(μ-S-Cys)$_2$(dipy)$_2$]Cl$_2$, MW 750.67 g/mol, %: C, 41.60; N, 11.19; Cu, 16.93; S, 8.54.

IR spectrum (KBr pellets), $v_{max}$, cm$^{-1}$: 520, 691, 815, 879, 1058, 1133, 1212, 1229, 1254, 1343, 1404, 1572, 1594, 1627, 2655, 2925, 2940, 2971, 3119, 3480.

The preparation can be synthesized without a stage of isolation of the coordination compound in the solid phase: the calculated amount of Cu(2,2'-dipy)Cl$_2$ is added to an aqueous solution containing a double or more excess amount of cysteine. The resultant solution can be used to obtain preparations.

Example No. 6

Obtaining a preparation comprising lithium ions and a binuclear coordination compound of copper with cysteine.

0.1 g of [Cu$_2$(μ-S-Cys)$_2$(dipy)$_2$]Cl$_2$ (Example No. 5) was added to an aqueous solution (~150 ml) containing 16.14 g of cysteine (molar ratio of coordination compound to thiol 1:1000) and thoroughly stirred. Lithium hydroxide monohydrate LiOH.H$_2$O was then added to the resultant solution in small portions and stirring was continued until it was fully dissolved, after which the pH of the resultant solution was adjusted to 7.2-7.4 with saturated LiOH solution.

The substance was ready for use after sublimation drying under vacuum.

Example No. 7

Obtaining a preparation comprising thioctic acid and a binuclear coordination compound of palladium with acetylcysteine.

The preparation is obtained by mixing aqueous solutions containing the calculated amounts of [Pd$_2$(μ-S-Accys)$_2$(dipy)$_2$]Cl$_2$.H$_2$O (Example No. 3) and lipoic (thiooctic) acid in a molar ratio of 1:1000.

The substance is ready for use after sublimation drying of the solution under vacuum.

Example No. 8

Obtaining a preparation comprising adenosine and a binuclear coordination compound of palladium with acetylcysteine.

The preparation is obtained by mixing aqueous solutions containing the calculated amounts of [Pd$_2$(μ-S-Accys)$_2$(dipy)$_2$]Cl$_2$.H$_2$O (Example No. 3), acetylcysteine and adenosine in a molar ratio of 1:1000:1.

The substance is ready for use after vacuum-sublimation drying of the solution.

Example No. 9

Enhancing the affinity of a pharmacological target—the epidermal growth factor receptor—to the action of tyrosine-kinase activity inhibitors by means of a coordination compound.

A causative link has been demonstrated clinically between enhanced HER1 and HER2/neu activity and the malignant growth of tumor cells in cancer of the breast, lungs, ovary, bone and esophagus. In this connection, the epidermal growth factor receptor (EGFR) is one of the objects which are being studied actively as an anti-tumor target [5, 7].

A number of pharmacological solutions exist which are directed at blocking the biological effect realized via the EGFR:

1) the use of monoclonal antibodies, which bind to the extracellular part of the receptor: Erbitux—monoclonal antibodies to HER1, Herceptin—monoclonal antibodies to HER2/neu; 2) the use of recombinant peptide ligands EGF and/or TGF-a, conjugated with cell penetrating cytotoxins; 3) the use of low-molecular inhibitors capable of acting on the intracellular domain of EGFR and interrupting the process of tyrosine-kinase phosphorylation of signal-transmitting proteins—Iressa, tyrphostins, genistein, SU6668, ZD6474.

The interaction of antibodies with the immune activity center of a receptor, and of inhibitors with an active center of catalytic activity requires that these centers be accessible, and this in its turn is determined by the conformation of the protein molecule. The conformation of the dimeric EGFR molecule makes it possible for tyrosine-kinase inhibitors and monoclonal antibodies to interact with their binding sites.

Object of the work. To study the effect of a coordination compound on the affinity of a pharmacological target—the epidermal growth factor receptor—to the action of a tyrosine-kinase activity inhibitor.

The test compounds used were a coordination compound of cysteine and palladium (C—Pd), cysteine (C), the coordination compound C—Pd with an excess of cysteine (C—Pd:

C, coordination compound:cysteine ratio 1:1000), a physiological high-affinity ligand of the EGF receptor—epidermal growth factor, and tyrphostin AG 1478 (Sigma, USA), an EGF tyrosine-kinase receptor inhibitor.

Obtaining Preparations for Performing the Studies.

The test compounds were stored at +4° C.; substances were dissolved in deionized water (super Q) immediately before commencing an experiment. The concentration of the initial solution exceeds by 1000 times or more the concentrations used in the experiment. The prepared concentrated solution is stored for not more than 5 hours at +4° C.

Administration Route.

Compounds were added to the cell culture medium to the final test concentration.

Number of Doses.

A preparation is added to cells in a single dose for the indicated period of time.

Concentrations.

Cysteine (C) 0.015 and 0.15 μmmol/ml;

Cysteine coordination compound—C—Pd, 0.015 and 0.15 nmol/ml;

Cysteine coordination compound: cysteine (C—Pd:C) 1:1000 0.015 and 0.15 μmol/ml (ligand concentration given in μmol/ml).

Epidermal growth factor 200 ng/ml.

EGF tyrosine-kinase receptor inhibitor—tyrphostin AG1478 in concentrations of 0.1 μg/ml, 0.25 μg/ml, 0.5 μg/ml, 0.75 μg/ml, 1.0 μg/ml, 2.5 μg/ml, 5 μg/ml, 7.5 μg/ml, 10 μg/ml.

Preparations were added in a single dose.

Time of determination of tyrosine-kinase activity of epidermal growth factor receptor: 0 min, 5 min, 10 min, 30 min, 1 h, 2 h, 4 h, 8 h.

The number of living and dead cells in a culture was determined after 24 and 48 hours.

Cell Line Used.

A431 line human epidermoid carcinoma cells, obtained from the All-Russian Cell Culture Collection (Russian Academy of Sciences Institute of Cytology, St. Petersburg).

Cell Culture Conditions.

Cells are cultured in a $CO_2$ incubator (New Brunswick Scientific) at +37° C. and with a $CO_2$ content of 5%. Cells are grown in these conditions to a monolayer culture and are exposed to the action of the test compounds.

Cell Culture Medium.

The DMEM medium (OOO PanEko, Moscow) with the addition of gentamicin K (80 mg/l), L-glutamine (300 mg/l) and fetal serum (PAA, Austria) to a final concentration of 10%, is used for culturing cells. Cells are transferred to a medium with a reduced serum content of 0.5% 24 hours before commencing an experiment.

Cell Growth Dynamics.

A431 cells were plated on plastic Petri dishes (Nunc) in a concentration of $10000/cm^2$, and were exposed to the action of the test preparations after 24 hours, on forming a 10-15% monolayer.

Preparation of Cells for Staining.

The culture medium of the A431 cells was collected in test tubes (Falkon) for full analysis of detached dead cells, while the cells in Petri dishes were washed with PBS (which was combined with the collected medium) and treated with 0.25% trypsin solution in Versene (Paneko) for about 10 min at room temperature until the cells were detached. The cells were then suspended by pipetting with an automatic pipette and were combined with the previously collected medium. Samples were centrifuged at room temperature for 5 min at 400 g, the supernatant was removed and the deposit was resuspended in pH 7.4 PBS phosphate-salt buffer.

Staining Cells with Propidium Iodide.

Propidium iodide was added to a suspension of cells to a concentration of 50 μg/ml 5-10 min before measuring in a Bruker ACR 1000 flow cytofluorimeter. This stain is able to penetrate through a damaged cell membrane, and stained cells are dead.

Cell Lysing Method.

After completing stimulation, cells are washed with phosphate-salt buffer (pH 7.4) in ice. In order to obtain a total lysate, cells are scraped in a buffer containing 20 mM Tris, pH 7.4, 150 mM NaCl, 1 mM $Na_3VO_4$, 1 mM EDTA, 1 mM EGTA, 0.5 mM PMSF, 1 μg/ml each of leupeptin, aprotinin and pepstatin, 0.5% Nonidet P-40 and 1% Triton X-100, and are incubated for 10 min at 4° C. The resultant material is passed 5 times through a 26 G needle and is centrifuged for 5 min at 10000 g. ¼ volume of buffer for electrophoretic samples (40 mM Tris, pH 6.8, 10% SDS, 20% 2-mercaptoethanol, 40% glycerol, 0.05% bromophenol blue) is added to the supernatant, stirred and heated for 5 min at 100° C.

Determination of Protein Concentration.

The concentration of protein in the samples before electrophoresis is determined using RC-DC Protein Assay (BioRad) reagents in a BioMate 3 (Thermo Electron Corporation) spectrophotometer.

Electrophoresis and Electrotransfer.

Electrophoretic separation of the proteins is carried out in 7.5% polyacrylamide gel for analysis of epidermal growth factor receptor and in 12% gel for analysis of MAP kinases ERK 1, 2 using the standard method. Samples containing an equal amount of protein are applied to the gel. Subsequent electrotransfer of the separated proteins to a nitrocellulose membrane (Hybond ECL, Amersham) is carried out in a buffer containing 0.58% Tris, 0.29% glycine, 0.035% Na dodecylsulfate and 20% methanol. Ponceau S (Sigma) is used to visualize the protein bands.

Immunoblotting.

Immunoblotting is carried out in accordance with the Western Blotting protocols ECL method (Amersham). All procedures are carried out at room temperature. The nitrocellulose membrane is washed in a solution containing 10 mM Tris, pH 7.6, 100 mM NaCl and 0.1% Tween 20 (TBS-T) for 10 min. The membrane is then incubated in a 1% solution of BSA (Sigma) or a 5% solution of skimmed milk (Valio) in TBS-T buffer for 1 h, and then in a solution of primary antibodies in TBS-T buffer for 1-1.5 h. The mertibrane is then washed in TBS-T 5 times, each for 5 min, placed in a solution of secondary antibodies in TBS-T buffer containing 5% skimmed milk, and incubated for 1 h. After washing the membrane (TBS-T, 5 times each of 5 min), the proteins bonded to antibodies are revealed using the enhanced chemiluminescence method. The nitrocellulose membrane is incubated in ECL (Amersham) solution at a rate of $0.125 ml/cm^2$ for 1 min and the chemiluminescent light is recorded by exposure on Kodak X-OMAT AR X-ray film.

Antibodies.

Primary monoclonal antibodies against phosphotyrosine (PY20, Transduction Laboratories, USA) and polyclonal rabbit antibodies against ERK 1, 2 phosphorylated on the tyrosine (Cell Signaling Technology, USA) are used for specific detection of proteins on the membrane. Polyclonal rabbit antibodies against the EGF receptor, and polyclonal rabbit antibodies against ERK 1, 2 (Cell Signaling Technology, USA) are used for additional identification of the detected active forms of the test proteins in the course of the work.

Goat antibodies obtained against mouse immunoglobulins and conjugated with peroxidase (GAM-HRP) (Sigma, USA), and goat antibodies developed against rabbit immunoglobulins and conjugated with horse radish peroxidase (GAR-HRP, Cell Signaling Technology, USA) are used as secondary antibodies in immunoblotting. Primary polyclonal rabbit antibodies against hemoxygenase 1 (Santa Cruz, USA) are used for specific detection of hemoxygenase. Antibodies obtained against rabbit immunoglobulins and conjugated with peroxidase (GAR-HRP) (Santa Cruz, USA) are used as secondary antibodies in immunoblotting.

Method for Removing Antibodies from the Membrane (Stripping).

In order to remove antibodies attached to the nitrocellulose membrane and to re-stain it with other antibodies, the membrane is incubated in a solution containing 60 mM Tris-HCl (pH 6.8), 2% SDS and 100 mM 2-mercaptoethanol for 30 min at 50° C. with rocking.

Methods for Densitometry and Statistical Processing of Results.

X-ray films with results were scanned using the Photoshop 6.0 program, densitometry of bands was carried out using the Scion Image 4.0.2. program, and the values obtained were divided by the control value and were averaged for three analogous experiments (repeats). Graphics were drawn using the Microsoft Excel 2000 9.0 program, placing time on the X-axis and the ratio of the experimental values to the control value on the Y axis.

Results of the Effect of the Test Compounds on Cell Proliferative Activity and Death According to the results obtained, in the concentrations employed, cysteine produces an 8- to 10-fold activation of the EGF receptor during prolonged periods of action of from 1 h to 4-8 hours as compared to the control series values.

In the concentrations employed, the coordination compound C—Pd has an effect on the tyrosine-kinase activity of the epidermal growth factor receptor which is 5 to 8 times stronger during the first hour and 15 to 20 times stronger during prolonged periods of action of from 1 hour to 4-8 hours as compared to the control series values.

In the concentrations employed and the periods of time analyzed, when using the combined action of cysteine and the coordination compound of cysteine—C—Pd:C—1:1000, the profile of the tyrosine-kinase activity of the epidermal growth factor receptor was similar to the profile of the tyrosine-kinase activity of the EGF receptor under the influence of the coordination compound. The level of the tyrosine-kinase activity of the EGF receptor under the influence of C—Pd:C showed a slight increase over prolonged periods of action of from 1 hour to 4-8 hours, averaging about 20% compared to the level of the activating influence on the receptor of the coordination compound alone.

The greatest increase in the tyrosine-kinase activity of the EGF receptor occurred under the influence of the high-affinity ligand of the EGF receptor—epidermal growth factor—in saturating concentration, when it was 2 to 3 times greater than the tyrosine-kinase activity of the EGF receptor under the influence of the coordination compound in the early period (up to 1 hour) and 4 to 5 times greater at from 1 hour to 4-8 hours.

The EGF receptor tyrosine-kinase inhibitor tyrphostin AG1478 completely inhibits the tyrosine-kinase activity of the EGF receptor in a culture of A431 cells in concentrations of from 3 to 7 µg/ml when introduced 10-25 min before the action of the high-affinity ligand epidermal growth factor.

When determining the optimal time for introducing the inhibitor, it was used in a concentration of 7.5 µg/ml. The inhibitor was introduced 1, 5, 10, 15, 20, 25 and 30 min before adding epidermal growth factor (200 ng/ml) to the incubation medium. The inhibitor completely eliminated stimulation of the tyrosine-kinase activity of the EGF receptor by epidermal growth factor in all the series of experiments at early and late times when acting for 15, 20, 25 and 30 min before the action of the epidermal receptor ligand. When the AG1478 inhibitor acted for 10 min before exposure to epidermal growth factor the receptors retained 10-15% of the tyrosine-kinase activity at late determination times (1 hour, 4 and 8 hours). Because of this, 15 min was chosen as the minimum time for the action of the tyrphostin AG1478 inhibitor before exposure to epidermal growth factor. When determining the doses of tyrphostin AG1478 which exhibit and do not exhibit an inhibiting effect on the tyrosine-kinase activity of the EGF receptor, it was used in concentrations of 0.1 µg/ml, 0.25 0.5 µg/ml, 0.75 µg/ml, 1 µg/ml, 2.5 µg/ml, 5 µg/ml, and 7.5 µg/ml. AG 1478 reduced the tyrosine-kinase activity of the EGF receptor by 30% in a concentration of 2.5 µg/ml, while when acting in a concentration of 5 µg/ml and 7.5 µg/ml no EGF receptor tyrosine-kinase activity was detected. When the AG 1478 inhibitor of EGF receptor tyrosine-kinase activity was used in concentrations of 0.1 µg/ml, 0.25 µg/ml, 0.5 µg/ml and 0.75 µg/ml it did not affect the manifestation of EGF receptor tyrosine-kinase activity initiated by the high-affinity ligand epidermal growth factor. When the AG1478 inhibitor of EGF receptor tyrosine-kinase activity was used in a concentration of 1 µg/ml, a statistically non-reliable increase in the tyrosine-kinase activity of the EGF receptor was detected in the late stages of incubation (1, 4 and 8 hours).

The experimental results obtained testify to the formation of an EGF receptor dimer under the influence of a coordination compound in the concentrations employed, and enhancement of the effect of the coordination compound when it is combined with an excess of ligand, since it is known that only the EGF receptor dimer possesses tyrosine-kinase activity. Enhancement of the activity of the coordination compound when it is combined with an excess of ligand may be due to a large amount of the coordination compound entering the incubation medium. Work with small concentrations is hazardous in that part of the substance may be lost as a consequence of sorption on the walls of vessels and pipettes. Such losses are very slight, but when using substances in ultra-small amounts may lead to virtually complete loss of the substance before it is introduced into the cell incubation medium. An excess of the organic molecule in such a case facilitates addition of the planned concentration of the test substance to the incubation medium. This argument does not cancel out the experimental fact of the inherent effect of cysteine on the tyrosine-kinase activity of the EGF receptor, but does not answer the question of whether such a change in the activity of cellular reactions, controlled by means of action on the EGF receptor, is significant for the cell, or whether it is a consequence of transactivation of the EGF receptor, which occurs when many substances act on a cell and is not associated with a direct physiological function thereof. It is known that a change in proliferative activity is a reflection of the specificity of an inhibiting or activating action on the EGF receptor. In this connection, change in proliferative activity during the action of the test compounds was evaluated (Table 2).

TABLE 2

Effect of the test compounds on the roliferative activity of A431 cells

| Test compound/concentration | Age of culture (hours) | Total cells (×10³/ml) | Proportion of dead cells (%) |
|---|---|---|---|
| Control (without addition of test compounds) | 0 | 10.0 | — |
|  | 24 | 14.3 | 12 |
|  | 48 | 21.1 | 19 |
| Cysteine - 0.015 μmol/ml | 0 | 10.0 | — |
|  | 24 | 14.7 | 11 |
|  | 48 | 23.5 | 22 |
| Coordination compound of cysteine-C—Pd 0.015 nmol/ml | 0 | 10.0 | — |
|  | 24 | 32.3 | 8 |
|  | 48 | 36.1 | 12 |
| Coordination compound of cysteine:cysteine (C—Pd:C) 1:1000 0.015 μmol/ml | 0 | 10.0 | — |
|  | 24 | 34.3 | 11 |
|  | 48 | 39.1 | 10 |
| Epidermal growth factor 200 ng/ml. | 0 | 10.0 | — |
|  | 24 | 47.3 | 19 |
|  | 48 | 68.8 | 23 |
| Epidermal growth factor 200 ng/ml + AG1478* 0.75 μg/ml | 0 | 10.0 | — |
|  | 24 | 48.1 | 20 |
|  | 48 | 70.8 | 25 |
| Epidermal growth factor 200 ng/ml + AG1478 1.0 μg/ml | 0 | 10.0 | — |
|  | 24 | 47.1 | 23 |
|  | 48 | 65.7 | 23 |
| Epidermal growth factor 200 ng/ml + AG1478 2.5 μg/ml | 0 | 10.0 | — |
|  | 24 | 39.4 | 27 |
|  | 48 | 61.1 | 30 |
| Epidermal growth factor 200 ng/ml + AG1478 5.0 μg/ml | 0 | 10.0 | — |
|  | 24 | 6.4 | 29 |
|  | 48 | 2.1 | 41 |

*AG1478 was introduced 15 min before the action of epidermal growth factor.

The results of the experiments show virtually identical proliferative activity of the cells in the control and under the influence of cysteine, which indicates that cysteine has no effect on stimulation of proliferative activity. In contrast, a coordination compound of cysteine and palladium stimulates the proliferative activity of A431 cells whatever the method of use, independently or in an excess of ligand. The result obtained indicates that a coordination compound of a d-metal and a sulfur-containing organic molecule possesses an inherent biological effect which cannot be the same as the inherent effect of the ligand. Such a difference may be due to the manifestation of a new property or properties of the coordination compound which are not intrinsic to the ligand. Epidermal growth factor has the maximum stimulating effect on the proliferative activity of A431 cells. The results of combined use with a tyrosine-kinase activity inhibitor made it possible to elucidate the concentrations in which its inhibiting activity is insufficient. It is known that the affinity of the inhibitor for the binding site is maximal for the dimeric form of the EGF receptor molecule, and it may be hypothesized that preincubation with the inhibitor leads to the bonding of AG1478 with those molecules of the EGF receptor which are in the dimeric form, but that the remaining inhibitor molecules are insufficient, on dimerization of the receptor due to the action of epidermal growth factor, to bond with the tyrosine-kinase activity center before phosphorylation by this of specific tyrosines. In this connection, it is logical to check the result of the action of ineffective concentrations of AG1478 inhibitor (1.0 μg/ml, 2.5 μg/ml) in the case where dimerization of the receptor is initiated by the action of a coordination compound (the coordination compound was used in an excess of ligand, taking into account that the latter has no effect on proliferative activity and that accurate dosing of the coordination compound is possible in such a combination). In this case, the inhibitor molecules will be able to bond maximally with the dimerized receptors and eliminate subsequent tyrosine-kinase activity of the EGF receptor during the action of epidermal growth factor. A preincubation time of 30 min before introduction of inhibitor was chosen to allow for the maximum stimulating effect of the coordination compound in an excess of ligand on the tyrosine-kinase activity of the EGF receptor in the early period, and incubation with AG1478 inhibitor concentrations of 1.0 μg/ml and 2.5 μg/ml was 15 min before the action of epidermal growth factor. The results of the experiment are presented in Table 3.

TABLE 3

Influence of a coordination compound on the effectiveness of EGF receptor inhibitor AG1478

| Test compound/concentration | Age of culture (hours) | Total cells (×10³/ml) | Proportion of dead cells (%) |
|---|---|---|---|
| Control (without addition of test compounds) | 0 | 10.0 | — |
|  | 24 | 15.2 | 11 |
|  | 48 | 23.3 | 17 |
| Epidermal growth factor 200 ng/ml. | 0 | 10.0 | — |
|  | 24 | 52.0 | 22 |
|  | 48 | 71.7 | 29 |
| Coordination compound of cysteine:cysteine (C—Pd:C) 1:1000 0.015 μmol/ml + AG1478 1.0 μg/ml + EGF | 0 | 10.0 | — |
|  | 24 | 27.4 | 24 |
|  | 48 | 29.1 | 31 |
| Coordination compound of cysteine:cysteine (C—Pd:C) 1:1000 0.015 μmol/ml + AG1478 2.5 μg/ml + EGF | 0 | 10.0 | — |
|  | 24 | 8.1 | 26 |
|  | 48 | 5.4 | 29 |

It follows from the results obtained that the effect of the coordination compound on the EGF receptor makes it possible to enhance the effectiveness of the action of the AG 1478 tyrosine-kinase activity inhibitor and when used in combination to use the latter in smaller concentrations.

Knowing that the EGF receptor is a target of pharmacological action, and taking into account the ability of binuclear coordination compounds of d-elements with aliphatic thiols to enhance the affinity of the EGF receptor to a means of pharmacological action, the tyrosine-kinase activity inhibitor, it may be hypothesized that the use of binuclear coordination compounds of d-elements with aliphatic thiols makes it possible to move on to the treatment of diseases, where enhancing the sensitivity of a pharmacological target to the action of a drug for use of the latter in physiologically adequate doses is significant.

Example No. 10

Increasing the concentration of a drug in the microenvironment of a pharmacological target by inhibiting a multiple drug resistance factor—P-glycoprotein—by the action of a coordination compound.

P-glycoprotein (Pgp) protects cells against molecules of toxic substances, including drug molecules, removing them from the cell and from the intracellular target. Many types of tumors are characterized by a marked resistance to the action of cytostatics as a result of the marked activity of Pgp at the cells which form these tumors. In this connection, the use of Pgp activity inhibitors in chemotherapeutic practice has found practical application in the treatment of malignant neoplasms for suppressing the drug resistance of the tumor cells. The use of Pgp inhibitors is restricted mainly to malignant neoplasms, due to the side-effects of Pgp inhibitors, which are more dangerous than the positive effect achieved from the action of the drug. Malignant neoplasms are an exception, since tumor cell resistance when using cytostatics indicates that no result will be achieved from chemotherapy and that large amounts of cytostatics will act on normal cells and will have a toxic effect thereon. In this connection it is justified to use Pgp inhibitors which make it possible to achieve a therapeutic effect from chemotherapeutic means, and to overcome the drug resistance of tumor cells due to Pgp. The search for new, low-toxicity, but effective inhibitors of P-glycoprotein is an urgent task, a solution to which will make it possible to enhance the effectiveness of pharmaceutical preparations in various diseases, including malignant neoplasm.

Object of the work: to study the ability of a coordination compound to increase the amount of a drug in the microenvironment of a target by inhibiting the activity of P-glycoprotein.

The test compounds used were a coordination compound of cysteamine and palladium (Ts-Pd) (Example No. 2); cysteamine (Ts); the coordination compound Ts-Pd with an excess of cysteamine (Ts-Pd:Ts; coordination compound: cysteamine ratio 1:1000) and doxorubicin, used in three concentrations: maximum—$5 \times 10^{-7}$M, and also 5 and 10 times less.

Obtaining Preparations for Performing the Studies.

The test compounds were stored at +4° C.; substances were dissolved in deionized water (super Q) immediately before commencing an experiment. The concentration of the initial solution exceeds by 1000 times or more the concentrations used in the experiment. The prepared concentrated solution is stored for not more than 5 hours at +4° C.

Administration Route.

Compounds were added to the cell culture medium to the final test concentration.

Number of Doses.

A preparation is added to cells in a single dose for the indicated period of time.

Concentrations.

Cysteamine (Ts) 0.015 and 0.15 umol/ml;

Cysteamine coordination compound—Ts-Pd, 0.015 and 0.15 nmol/ml;

Cysteamine coordination compound: cysteamine (Ts-Pd: Ts) 1:1000-0.015 and 0.15 μmol/ml (ligand concentration given in μmol/ml).

Preparations were added in a single dose.

Cell Line Used.

A culture of Jurkat line human T-lymphoblastic leukemia cells.

Cell Culturing Conditions.

Cells are cultured in a $CO_2$ incubator (New Brunswick Scientific) at +37° C. and with a $CO_2$ content of 5%. Cells are grown in these conditions to a monolayer culture and are exposed to the action of the test compounds.

Cell Culturing Conditions, Procedure for Determining the Effect of the Test Compounds on Pgp Activity Cells were cultured in RPMI-1640 medium containing 10% embryonic calf serum. On the day of an experiment, a suspension of cells was centrifuged for 10 minutes at 1.5 thousand rev/min and the deposit was resuspended in pH 7.4 phosphate buffer. The number of cells in the resultant suspension was counted in a Goryayev chamber and, where necessary, was centrifuged and resuspended in an appropriate volume of phosphate buffer until a final cell concentration of 1 million per ml was achieved.

The required dilutions of commercial antibodies were prepared, using pH 7.4 phosphate buffer, immediately before performing an experiment to study the effect of the test compounds on the interaction of monoclonal antibodies with markers of multiple drug resistance. The appropriate dilutions of antibodies were added to 100 μl of a suspension of the test cells with a specific concentration in plastic tubes for a flow cytofluorimeter, then incubated cold at 4° C. for 30 minutes. In order to wash out the free (not bonded to Pgp) antibodies after completing the incubation, 2 ml of pH 7.4 phosphate buffer were added to each tube and these were then centrifuged at 1.5 thousand rev/min for 10 min. The supernatant liquid was removed using a vacuum pump and the washing procedure was repeated. The deposit was resuspended in 300 μl of pH 7.4 phosphate buffer.

FITC-labeled clone 17F9 mouse monoclonal antibodies from BD Pharmingen were used in the work. These antibodies are characterized by specificity to the external epitope of the human transmembrane protein Pgp. Nine concentrations of the antibodies were used in the study, expressed in volumetric units of undiluted commercial solution: 40; 20; 10; 5; 2.5; 1; 0.5; 0.25; and 0.1 μl per 100 μl of cell suspension. A concentration of 40 μl was used as the maximum, since only an insignificant increase in fluorescence and the percentage of stained cells occurred on further increase in the amount of antibodies.

FITC-labeled $IgG_{2b}$,k mouse monoclonal antibodies in concentrations equivalent to the specific antibodies were used as an isotype control.

Assessing the Functional Activity of Pgp in a Cell Culture Suspension Using Flow Cytofluorimetry Cells are washed free of nutrient medium by centrifuging at 2 thousand revs, the deposit is resuspended in Henk's solution with glucose and without phenol red, and the cell suspension is added to test tubes. A transporter(s) inhibitor is then added to the cell suspension and the tubes are incubated for 20 min (Henk's solution with 5 mM of glucose is added to a control sample). This is followed by incubation for 5 min at 37° with doxorubicin, after which the cells are fixed with 10% formalin. In the following stage, the prepared samples are analyzed by flow cytofluorimetry.

Flow Cytofluorimetry Method

Fluorescence was measured in a FACSCalibur (Becton Dickinson) flow cytofluorimeter with an excitation wavelength of 488 nm and an emission wavelength of 576 nm, a shutter value of 100 and a speed of 200 cells/s. The number of events analyzed was from 5 to 10 thousand. Histograms of cell distribution according to the intensity of fluorescence were analyzed using the WinMDI program using the indices of average fluorescence cumulatively over the entire cell suspension and separately in the fluorescence field of the isotype control (marker M2) and specific binding of antibodies to Pgp (marker M1), and also according to the number of marker M1 cells in the specific binding of monoclonal antibodies field, which was determined by the Kolmogorov-Smirnov method.

Results of the Effect of the Test Compounds on the Proliferative Activity and Death of Cells Before commencing the main stage of the studies, we characterized expression of the multiple drug resistance marker Pgp in a culture of Jurkat line human T-lymphoblastic leukemia cells, staining cells with specific antibodies to the extracellular epitope of Pgp in an antibody concentrations range of 0.1; 0.25; 0.5; 1.0; 2.5; 5.0; 10.0; 20.0, 40.0 μl. In the concentrations employed, the test compounds did not affect interaction with cells of the isotype antibodies used in staining Pgp in the antibody concentrations range of 0.1; 0.25; 0.5; 1.0; 2.5; 5.0; 10.0; 20.0, 40.0 μl.

Preincubation of cells with the coordination compound, and with the coordination compound in an excess of ligand in the concentrations employed reduced the average fluorescence of cells marked by specific antibodies to Pgp by a factor of 1.4-1.7-2.0 at concentrations of specific antibodies to Pgp of 2.5-5.0-10.0 µl respectively at concentrations of 0.15 nmol/ml and 0.15 µmol/ml, and by a factor of 1.8-1.7-1.9 at concentrations of 0.015 nmol/ml and 0.015 µmol/ml in a second experiment. Cysteamine did not affect the average fluorescence of cells in any of the concentrations employed.

Pgp activity was thus suppressed only under the influence of the coordination compound, used individually or in an excess of ligand.

The action of the coordination compound in concentrations of 0.015 and 0.15 µmol/ml on the intracellular accumulation and distribution between cytoplasm and nucleus of the model preparation and the doxorubicin fluorescent probe, used in three concentrations—maximum—$5 \times 10^{-7}$ M, and also 5 and 10 times less—led to a marked increase in the intracellular accumulation of doxorubicin after preincubation of cells with the coordination compound in both test concentrations. This was recorded as an increase in the intracellular fluorescence of doxorubicin at various concentration ratios of doxorubicin. By a factor of 1.3 with a coordination compound 0.15 µmol/ml:doxorubicin 1/10 ratio, and by a factor of 1.4-2.0-2.2 respectively with a coordination compound 0.015 µmol/ml: doxorubicin 1, 1/5 and 1/0 ratio.

Furthermore, an increase in the nuclear accumulation of doxorubicin and the bonding thereof with DNA was noted with a doxorubicin concentration of 1 and ⅕ under the influence of the coordination compound in a concentration of 0.15 µmol/ml, the result of which was a considerable (by a factor of 1.4 and 1.7 respectively) decrease in the intracellular fluorescence of doxorubicin.

An increase in drug concentration in the microenvironment of the pharmacological target is thus achieved by the action of the coordination compound on the multiple drug resistance factor P-glycoprotein, so that the coordination compound can be considered a promising means for improving the therapeutic effectiveness of a drug and the use thereof in therapeutically optimal doses.

Example 11

Effect of a copper coordination compound on the activity of enzymes of the second phase of detoxification of xenobiotics in animal liver cells.

Object of the work. To study the effect of coordination compounds on the activity of enzymes of the second phase of detoxification of xenobiotics in animal liver cells.

Cysteine (C) and coordination compounds of cysteine with copper (C—Cu) with an excess of cysteine (see Example 5) were used as the test compounds.

The study was carried out on random-bred male white rats weighing 140-160 g from the RAMN Rappolovo breeding centre, in which a hepatotoxic effect was produced by the subcutaneous injection of cyclophosphane (CP) in a dose of 20 mg/kg in physiological saline daily for a period of 10 days.

Four groups of experimental animals were established.

No. 1—intact animals which were given injections of the solvent of the test compounds (physiological saline) (solvent control);

No. 2—intact animals which were given CP and were then injected with physiological saline as the therapeutic means (control);

Experimental Groups:

No. 3—animals which were given the test compound cysteine (C) in physiological saline intraperitoneally in a dose of 10 mg/kg for 10 days, 30 min after administration of the toxicant CP.

No. 4—animals which were given cysteine (C) in combination with a coordination compound of cysteine and copper (C—Cu:C, cysteine:coordination compound ratio 1000:1) in physiological saline intraperitoneally in a dose of 10 mg/kg (amount of coordination compound $8.3 \times 10^{-8}$ M/kg) for 10 days, 30 min after administration of the toxicant CP.

Enzymes of the second phase of detoxification of xenobiotics in the cytosol fraction of liver cells were studied: glutathione-S-transferase (EC 2.5.1.18), glutathione peroxidase (EC 1.11.1.9), glutathione reductase (EC 1.6.4.2), glucose-6-phosphate dehydrogenase (EC 1.1.1.49).

Test Material

The cytosol fraction of liver cells.

Test Enzymes

Glutathione-S-transferase (EC 2.5.1.18), glutathione peroxidase (EC 1.11.1.9), glutathione reductase (EC 1.6.4.2), glucose-6-phosphate dehydrogenase (EC 1.1.1.49).

Method for Obtaining the Cytosol Fraction of Liver Cells

In order to obtain material for the studies, laboratory animals anesthetized with ether were decapitated. The liver was extracted after completely removing blood from it by perfusion of chilled 0.15 M KCl solution (pH 7.8) through the superior vena cava. Liver cells were separated from the stroma and homogenized in a Downs type homogenizer with a Teflon pestle, using a 1:10 ratio of the weight of tissue to the volume of solution (0.15 M KCl, pH 7.8). The homogenate was centrifuged at $12 \times 10^3$ g and a temperature of 4° C. for 25 min. The post-mitochondrial supernatant was centrifuged at $105 \times 10^3$ g and a temperature of 4° C. for 60 min using a Type 50 3.Ti rotor in an L8-M ultra-centrifuge (Beckman, USA). The cytosol fraction was used to determine the activity of the enzymes.

The concentration of reduced glutathione in the liver cell homogenate was determined using 5,5'-di-thio-bis(-2-nitrobenzoic) acid (DTNB) by the method of G. L. Ellman, using a solution of sulfosalicylic acid to precipitate protein in the samples which, in contrast to the use of metaphosphoric or trichloroacetic acids, eliminated spontaneous conversion of the reduced form of glutathione to the oxidized form.

The principle of the method is based on the reaction of DTNB (Ellman agent) with acid-soluble thiol groups of the colored product—5-thio-2-nitrobenzoic acid (TNB), which has maximum absorption at a wavelength of 412 nm.

0.2 ml of 20% sulfosalicylic acid solution was added to 0.6 ml of liver cell homogenate. Samples were centrifuged for 10 min at 3000 rev/min and a temperature of +2° C. 0.2 ml of the resultant supernatant was transferred to test tubes containing 2.55 ml of 0.1 M TRIS-HCl buffer with 0.01% ethylenediamine tetraacetate (EDTA), pH 8.5. 25; A of DTNB solution (4 mg of commercial DTNB preparation (Boehring Mannheim, Germany) in 1 ml of absolute methanol) were added to the resultant mixture. After development of the color, samples were measured in a DU 650 spectrophotometer (Beckman, USA) against a reference solution at a wavelength of 412 nm in a cell with an optical path length of 10 mm. The content of reduced glutathione was calculated using a calibration curve. For this purpose, solutions of RG with concentrations of from 0.02 to 2.0 mmol/l were prepared using a commercial RG preparation (Sigma, USA), samples were taken from these for determination of the content of reduced glutathione by the method described above, and a calibration curve was drawn from the extinction values obtained. The concentration of reduced glutathione was calculated using the calibration cure.

Determination of the Activity of the Enzymes.

Determination of the Activity of Glutathione Peroxidase (EC 1.11.1.9).

The activity of glutathione peroxidase was determined using tert-butyl hydroperoxide (TBHP) as the substrate.

The principle of the method comprises the utilization of reduced glutathione by glutathione peroxidase during the incubation of cell cytosol with TBHP. The content of reduced glutathione (RG) in samples before and after incubation was determined by a color reaction using 5,5'-di-thio-bis(-2-nitrobenzoic) acid (DRNB) by the method of G. L. Ellman.

In order to carry out the enzyme reaction, the cytosol fraction of liver cells was additionally diluted 40-fold with 0.1 M potassium-phosphate buffer, pH 7.4. 0.2 ml of diluted cytosol was placed in experimental and control samples and 0.73 ml of 0.1 M TRIS-HCl buffer, pH 8.5 was added (1 ml of buffer contains 0.1 mg of EDTA, 0.78 mg of $NaN_3$ (Sigma, USA) and 1 mg of RG (Sigma, USA)). Samples were incubated in a thermostat at +37° C. for 10 min. The reaction was started by introducing 70 µl of TBHP, prepared by diluting 500-fold in distilled water a 70% commercial preparation (ICN, USA). 70 µl of $H_2O$ were added to the control samples in place of TBHP solution. After incubating for 5 mM at +37° C., the reaction was stopped by adding 0.2 ml of 20% trichloroacetic acid solution to each test tube. The samples were centrifuged at 3000 g for 10 mM, and the supernatant was used for determination of the amount of reduced glutathione similarly to the method described above. Enzyme activity was calculated using a calibration curve on the basis of the difference in the amount of RG in the experimental and control samples, and was expressed in mmol/(min·g protein).

Determination of the Activity of Glutathione Reductase (EC 1.6.4.2).

The activity of glutathione reductase was determined by a method based on the catalytic NADP-H-dependent reaction of reduction of the oxidized form of glutathione to the reduced form, the intensity of which can be evaluated from the rate of reduction in the extinction of samples at a wavelength of 340 nm, at which the NADP-H solution has maximum light absorption:

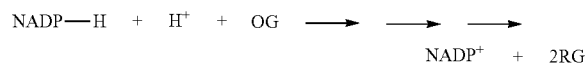

In order to perform the enzyme reaction, the cytosol fraction of liver cells was additionally diluted in a ratio of 1:9 with 0.1 M potassium-phosphate buffer, pH 7.4. The reaction was performed in a thermostatted cell at a temperature of +37° C. 1.8 ml of 0.1 M potassium-phosphate buffer, pH 7.0 with 1 mM of EDTA, 0.1 ml of 20 mM aqueous solution of oxidized glutathione (Boehringer Mannheim, Germany) and 100 µl of diluted cytosol fraction were placed in a cell. After 3-5 min of temperature equilibration, the reaction was started by the addition of 0.1 ml of a 2 mM solution of NADP-H (F. Hoffman—La Roche, Switzerland) dissolved in 10 mM TRIS-HCl buffer, pH 7.0. The optical density of the test solutions was measured at a wavelength of 340 nm against control samples immediately after stirring the contents for 5 min in a cell with an optical path length of 10 mm in a DU 650 spectrophotometer. Measurement of the optical density of a reaction mixture to which the same volume of 0.1 M potassium-phosphate buffer, pH 7.4, had been added in place of cytosol was used as the control. Glutathione reductase activity was calculated using the molar coefficient of light absorption for NADP-H at a wavelength of 340 nm, equal to $\epsilon=6200$ $M^{-1} \cdot cm^{-1}$. The activity was expressed in µmol/(min·g protein).

Determination of the Activity of Glutathione-5-Transferase (EC 2.5.1.18.)

The activity of glutathione-5-transferase was determined using the method of W. H. Habig and W. B. Jakoby.

The method is based on the ability of reduced glutathione to react with 1-chloro-2,4-dinitrobenzene in the presence of glutathione-5-transferase with formation of a product which has maximum light absorption at a wavelength of 340 nm.

In order to perform the enzyme reaction, the cytosol fraction of liver cells was additionally diluted in a ratio of 1:9 with 0.1 M potassium-phosphate buffer, pH 7.4. The reaction was performed in a thermostatted cell at a temperature of +37° C. 1.2 ml of a 2 mM solution of reduced glutathione (Sigma, USA) in 0.1 M potassium-phosphate buffer, pH 6.5, and 0.1 ml of diluted cytosol fraction were added to a cell. After temperature equilibration, the reaction was started by adding to the medium 1.2 ml of a 2 mM solution of 1-chloro-2,4-dinitrobenzene (10 mg of a commercial preparation (ICN, USA) were dissolved in 1 ml of absolute methanol, and 23 ml of 0.1 M potassium-phosphate buffer, pH 6.5, were added to the resultant alcohol solution). The optical density of the test solutions was measured at a wavelength of 340 nm against water immediately after mixing the contents and after 5 min, in a cell with an optical path length of 10 mm in a DU 650 spectrophotometer. Measurement of the optical density of a mixture to which the same volume of 0.1 M potassium-phosphate buffer, pH 7.4, had been added in place of cytosol was used as the control. The glutathione-5-transferase activity was calculated using a molar coefficient of light absorption at a wavelength of 340 nm for the product formed equal to $\epsilon=9600$ $M^{-1} \cdot cm^{-1}$. The activity was expressed in µmol/(min·g protein).

Determination of the Activity of Glucose-6-Phosphate Dehydrogenase (EC 1.1.1.49.)

The activity of glucose-6-phosphate dehydrogenase was determined using the method of A. Kornberg et al.

The method is based on the ability of glucose-6-phosphate dehydrogenase to reduce $NADP^+$ to NADP-H during the oxidation of glucose-6-phosphate. The amount of NADP-H formed is proportional to the enzyme activity.

The enzyme reaction was carried out in a thermostatted cell at a temperature of +37° C. 3.0 ml of 50 mM TRIS-HCl buffer, pH 7.6, with 5 mM of EDTA, 0.1 ml of a 10 mM solution of NADP (Merck, Germany) and 50 µl of liver cytosol fraction were placed in a cell. After temperature equilibration, the reaction was initiated by adding 0.1 ml of a 5 mM solution of glucose-6-phosphate sodium (Boehringer Mannheim, Germany) to the test medium. Samples were measured photometrically at a wavelength of 340 nm against a control without the substrate after 5 min in a cell with an optical path length of 10 mm in a DU 650 spectrophotometer. The activity was calculated using a molar coefficient of light absorption at a wavelength of 340 nm for the NADP-H formed equal to $\epsilon=6200$ $M^{-1} \cdot cm^{-1}$. The activity was expressed in µmol/(min·g protein).

Determination of Protein Concentration.

The protein content was determined by the Lowry method in the modification of G. L. Peterson.

The principle of the method comprises the performance of two successive reactions, specific for determination of protein: with copper tartrate-carbonate, which reacts in an alkaline medium with the peptide bond, and with Folin-Ciocalteu reagent, which reacts with aromatic aminoacids. This results in the formation of colored complexes which have maximum light absorption at a wavelength of 750 m, the intensity of the color being proportional to the protein content of the sample.

10 μl of liver cytosol fraction and 0.1 ml of 0.15% solution of sodium deoxycholate (Sigma, USA) were added successively to 0.99 ml of distilled water. Samples were incubated for 10 min at room temperature, then the protein in the samples was precipitated with 0.1 ml of 72% trichloroacetic acid solution. The samples were then centrifuged for 15 min at 3000 rev/min. The supernatant was removed and 1 ml of water and 1 ml of a reagent prepared from equal volumes of 10% sodium dodecylsulfate solution, 0.8 M NaOH solution, distilled water and a solution of copper tartrate-carbonate (0.1% copper sulfate, 0.2% potassium-sodium tartrate and 10% sodium carbonate) were added to the deposit. The deposit dissolved after the reagent was added to the deposit. The resultant solution was incubated at a temperature of +30° C. for 10 min. 0.5 ml of 0.33 M Folin-Ciocalteu reagent (Serva, Germany) was then added to the solution and after shaking the samples were left in a dark place for 30 min. The samples were then measured photometrically in a DU 650 spectrophotometer against distilled water at a wavelength of 750 nm in a cell with an optical path length of 10 mm. In order to determine the protein content a calibration curve was constructed, for which purpose aqueous solutions of bovine serum albumin were prepared with concentrations of from 0.1 to 10.0 g/l, samples were taken from these for determination of the protein content using the method described, and extinction values corresponding to specific concentrations were obtained. The content of protein in the cytosol fraction was calculated using the calibration curve and was expressed in g/l.

Statistical Processing of Results

The results obtained were processed statistically in a personal computer using the STATISTICA 6.0 software suite. The average values and the mean error were calculated in each group. The reliability of differences with the corresponding control group were assessed using the t-test. The values given in the text and tables are presented in the form $X_{av} \pm m_x$.

Results of the Study

The results of studying the complex of molecular reactions which provide tolerance to the action of toxic substances testify to the ability of cysteine (C) and a coordination compound thereof (C—Cu) to induce the activity of enzymes of the second phase of detoxification of xenobiotics—glutathione reductase (EC 1.6.4.2), glutathione peroxidase (EC 1.11.1.9), glutathione-5-transferase (EC 2.5.1.18), and also the metabolism of reduced glutathione associated therewith (Table 4).

TABLE 4

Effect of a coordination compound of cysteine and copper (see Example No. 5) on the ability of cysteine to induce the activity of enzymes of the second phase of detoxification of xenobiotics in the liver cells of randomly bred white rats on repeated administration of cyclophosphane in a dose of 20 mg/kg over a period of 10 days (activity of enzymes in μmol/(min · g protein), reduced glutathione in μmol/g protein)

| Study group | Values of analyzed characteristic | | | | |
| --- | --- | --- | --- | --- | --- |
|  | GR | GP | GST | G-6-PDG | GSH |
| Control | 271.3 ± 15.8 | 15.2 ± 0.4 | 2281 ± 187 | 181.6 ± 12.9 | 13.68 ± 0.62 |
| No correction | 175.3 ± 11.7 | 13.8 ± 0.2* | 1727 ± 86* | 86.2 ± 7.7* | 9.61 ± 0.02* |
| cysteine-copper:cysteine 1000:1 | 270.8 ± 12.6 | 27.9 ± 2.2* | 2857 ± 120* | 158.1 ± 13.3 | 11.21 ± 0.56* |

*reliability of difference p < 0.05 compared with control group
□reliability of difference p < 0.05 compared with group of animals receiving toxin without correction
GR - glutathione reductase (EC 1.6.4.2)
GP - glutathione peroxidase (EC 1.11.1.9)
GST - glutathione-S-transferase (EC 2.5.1.18)
G6PDG - glucoso-6-phosphate dehydrogenase (EC 1.1.1.49.)
GSH - reduced glutathione Ultra-small amounts of the coordination compounds enhanced the ability of cysteine to induce the activity of enzymes of the second phase of detoxification of xenobiotics, and increased the intensity of metabolism of the key metabolite reduced glutathione associated therewith.

The combined use of a binuclear coordination compound of a d-metal with an aliphatic thiol together with other etiotropic, pathogenetic and symptomatic treatment means will thus make it possible to avoid side-effects of the associated drug preparation, making treatment physiologically more adequate.

Example No. 12

The effect of a coordination compound of copper and acetylcysteine on the hemostimulating activity of the lithium salt of acetylcysteine.

A preparation containing the lithium salt of acetyl cysteine (aC-Li) and a coordination compound of copper (see Example No. 6) was studied.

Preparation of Solutions of the Test Compounds for Performing the Study.

The crystalline substances were stored at 4° C.; a substance was dissolved in physiological saline immediately before commencing an experiment. The solution was sterilized by passing through 0.22 μm Millex-GS (Millipore) filters in a sterile laminar-flow cabinet.

Study Model.

The study was carried out on random-bred male white rats weighing 140-160 g, which were given a single subcutaneous injection of cyclophosphane in a dose of 100 mg/kg in physiological saline.

Four groups of experimental animals were established.

No. 1—intact animals which were given injections of the solvent of the test compounds (physiological saline) (solvent control);

No. 2—intact animals which were given CP and were then injected with physiological saline as the therapeutic means (control);

Experimental Groups:

No. 3—animals which had received an injection of cyclophosphane and to which Cu-aC-Li:aC-Li in physiological saline was then administered in a dose of 10 mg/kg as a therapeutic means (amount of coordination compound $7.8 \times 10^{-8}$ M/kg);

No. 4—animals which had received an injection of cyclophosphane and to which aC-Li in physiological saline was then administered in a dose of 10 mg/kg as a therapeutic means;

No. 5—animals which had received an injection of cyclophosphane and to which lithium carbonate in physiological saline was then administered in a dose of 3 mg/kg as a therapeutic means (the amount of lithium carbonate was calculated on the basis of the proportion by weight of lithium ion (0.55) in 10 mg of the lithium salt of cysteine, the same amount of lithium is contained in 3 mg of lithium carbonate);

No. 6—animals which had received an injection of cyclophosphane and to which acetylcysteine in physiological saline was then administered in a dose of 9.5 mg/kg as a therapeutic means (the amount of acetylcysteine was calculated on the basis of the proportion by weight of acetylcysteine (~0.95) in 10 mg of acetylcysteine, which corresponds to 9.5 mg of the hydrogenated form of acetylcysteine).

The test preparations were administered on the third day after the administration of cyclophosphane.

Test Material.

Blood for hematological investigations was taken from the caudal vein 3, 7 and 14 days after administration of CP. At the end of each series (3, 7 and 14 days), the experimental animals were euthanized by an overdose of ether and blood was obtained from the caudal vein and bone marrow from the femur.

Characteristics Analyzed.

This study assessed the cellularity of the blood (the number of erythrocytes, thrombocytes, leukocytes, lymphocytes and neutrophils, and also the ESR) and bone marrow on 7-day administration of the test compounds to hemodepressed animals.

Results of the Study.

The results of the studies performed on blood cellularity are presented in Tables 1-3.

In a dose of 100 g/kg, cyclophosphane causes fairly pronounced cytopenia in relation to all formed elements of the blood with absolute and relative lymphopenia, maximally expressed on the fourteenth day (1-3).

The coordination compound Ci-aC-Li:aC-Li exhibits a marked hemostimulating effect, which was manifested in virtually complete restoration of blood cellularity. In contrast to the coordination compound of copper with the lithium salt of acetylcysteine, introduced in an excess of the lithium salt of acetylcysteine, the action of acetylcysteine, the lithium salt of acetylcysteine and lithium carbonate is manifested in the form of positive trends, which overall can be assessed as a hemostimulating effect (Tables 5-7).

TABLE 5

General analysis of the blood of male rats with cytopenia on day 3 after administration of cyclophosphane (100 mg/kg); not treated (injected with physiological saline), treated with a hemostimulator ($Li_2HCO_3$), the lithium salt of acetylcysteine (aC—Li) and the lithium salt of acetylcysteine in combination with a coordination compound of acetylcysteine with copper (aC—Li:Cu—aC—Li, Example No. 6)

| Test parameters | Intact (phys. saline) | Cyclophosphane (phys. saline) | Cyclophosphane (acetyl cysteine) | Cyclohosphane ($Li_2HCO_3$) | Cyclophosphane + aC—Li | Cyclophosphane + Cu—aC—Li:aC—Li |
|---|---|---|---|---|---|---|
| Hemoglobin, (g/l) | 15.2 ± 0.16 | 13.0 ± 0.2 | 13.2 ± 0.21 | 13.1 ± 0.19 | 12.9 ± 0.22 | 12.5 ± 0.25 |
| Erythrocytes, $10^{12}$/l | 6.7 ± 0.16 | 3.5 ± 0.19 | 3.0 ± 0.29 | 3.7 ± 0.21 | 4.0 ± 0.23 | 4.8 ± 0.15 |
| ESR, mm/h | 2.5 ± 0.85 | 2 ± 0.37 | 2.2 ± 0.30 | 2.4 ± 0.42 | 3.3 ± 0.80 | 3.2 ± 0.54 |
| Thrombocytes, $10^9$/l | 374 ± 28.5 | 231 ± 35.3 | 220 ± 45.3 | 256 ± 45.3 | 387 ± 17.4 | 502 ± 36.4** |
| Reticulocytes, % | 1.8 ± 0.2 | 0.08 ± 0.005* | 0.09 ± 0.006* | 0.118 ± 0.01* | 0.1 ± 0.1** | 0.5 ± 0.1** |
| Leukocytes, $10^9$/l | 9.2 ± 0.35 | 3.58 ± 0.26* | 3.26 ± 0.31* | 3.75 ± 0.46* | 4.38 ± 0.31* | 4.49 ± 0.29* |
| Segmented neutrophils, % | 16 ± 2.5 | 18.7 ± 2.4* | 17.6 ± 2.1* | 19.7 ± 3.4* | 42 ± 1.6** | 38 ± 1.6** |
| Lymphoctes, % | 75.5 ± 1.4 | 71 ± 1.8* | 68 ± 2.8* | 62 ± 3.8* | 45 ± 1.6* | 51.3 ± 0.** |

*p 0.05 - in comparison with the biological control;
**p 0.05 - in comparison with the cyclophosphane control

TABLE 6

General analysis of the blood of male rats with cytopenia on day 7 after administration of cyclophosphane (100 mg/kg); not treated (injected with physiological saline), treated with a hemostimulator ($Li_2HCO_3$), the lithium salt of acetylcysteine (aC—Li) and the lithium salt of acetylcysteine in combination with a coordination compound of acetylcysteine with copper (aC—Li:Cu—aC—Li, Example No. 6).

| Test parameters | Intact (phys. Saline) | Cyclophosphane | Cyclophosphane (acetyl cysteine) | Cyclophosphane ($Li_2HCO_3$) | Cyclophosphane ($Li_2HCO_3$) | Cyclophosphane + Cu—aC—Li:aC—Li |
|---|---|---|---|---|---|---|
| Hemoglobin (g/l) | 15.2 ± 0.16 | 13.8 ± 0.56 | 13.4 ± 0.76 | 12.8 ± 0.44 | 13.2 ± 0.68 | 13.9 ± 0.31 |

TABLE 6-continued

General analysis of the blood of male rats with cytopenia on day 7 after administration of cyclophosphane (100 mg/kg); not treated (injected with physiological saline), treated with a hemostimulator (Li$_2$HCO$_3$), the lithium salt of acetylcysteine (aC—Li) and the lithium salt of acetylcysteine in combination with a coordination compound of acetylcysteine with copper (aC—Li:Cu—aC—Li, Example No. 6).

| Test parameters | Intact (phys. Saline) | Cyclo-phosphane | Cyclo-phosphane (acetyl cysteine) | Cyclo-phosphane (Li$_2$HCO$_3$) | Cyclo-phosphane (Li$_2$HCO$_3$) | Cyclo-phosphane + Cu—aC—Li:aC—Li |
|---|---|---|---|---|---|---|
| Erythrocytes 10$^{12}$/l | 6.7 ± 0.16 | 3.5 ± 0.25 | 3.1 ± 0.33 | 3.6 ± 0.29 | 3.2 ± 0.18 | 6.1 ± 0.08* |
| ESR, mm/h | 2.5 ± 0.85 | 1.8 ± 0.31 | 1.9 ± 0.39 | 2.0 ± 0.36 | 3.2 ± 0.80 | 2.0 ± 0.37 |
| Thrombocytes, 10$^3$/l | 374 ± 28.5 | 126 ± 10.0** | 124 ± 11.0** | 119 ± 12.0** | 164 ± 10.0** | 228 ± 13.8* |
| Reticulocytes, % | 1.8 ± 0.2 | 1.0 ± 0.1 | 0.9.0 ± 0.2 | 1.1 ± 0.1 | 1.2 ± 0.2 | 1.63 ± 0.2* |
| Leukocytes, 10$^9$/l | 9.2 ± 0.35 | 3.41 ± 0.09* | 3.47 ± 0.08* | 3.22 ± 0.11* | 4.8 ± 0.18** | 6.88 ± 0.18 |
| Segmented neutrophils, % | 16 ± 2.5 | 32 ± 1.9* | 30 ± 1.8* | 33 ± 1.7* | 50.4 ± 0.6** | 63.3 ± 1.6 |
| Lymphocytes, % | 75.5 ± 1.4 | 57.7 ± 1.1* | 51.5 ± 1.3* | 50.7 ± 1.6* | 22 ± 0.9* | 61 ± 0.9)* |

*p 0.05 - in comparison with the biological control;
**p 0.05 - in comparison with the cyclophosphane control

TABLE 7

General analysis of the blood of male rats with cytopenia on day 14 after administration of cyclophosphane (100 mg/kg); not treated (injected with physiological saline), treated with a hemostimulator (Li$_2$HCO$_3$), the lithium salt of acetylcysteine (aC—Li) and the lithium salt of acetylcysteine in combination with a coordination compound of acetylcysteine with copper (aC—Li:Cu—aC—Li) used in a ratio of 1000:1

| Test parameters | Intact (phys. saline) | Cyclo-phosphane | Cyclo-phosphane (acetyl cysteine) | Cyclo-phosphane (Li$_2$HCO$_3$) | Cyclo-phosphane + aC—Li | Cyclo-phosphane + Cu—aC—Li:aC—Li |
|---|---|---|---|---|---|---|
| Hemoglobin, (g/l) | 15.2 ± 0.16 | 12.3 ± 0.68 | 12.5 ± 0.5 | 13.1 ± 0.57 | 13.6 ± 0.63 | 13.7 ± 0.64 |
| Erythrocytes, 10$^{12}$/l | 6.7 ± 0.16 | 4.4 ± 0.17 | 4.7 ± 0.21 | 4.9 ± 0.27 | 5.2 ± 0.26 | 6.0 ± 0.12 |
| ESR, mm/h | 2.5 ± 0.85 | 2.3 ± 0.61 | 2.1 ± 0.73 | 2.4 ± 0.65 | 2.7 ± 0.49 | 2.8 ± 0.70 |
| Thrombocytes, 10$^3$/l | 368 ± 21.5 | 393 ± 56.9 | 387 ± 54.9 | 401 ± 59.9 | 390 ± 38.3 | 598 ± 72.9** |
| Reticulocytes, % | 1.8 ± 0.2 | 1.2 ± 0.2 | 1.1 ± 0.4 | 1.4 ± 0.3 | 1.3 ± 0.3 | 2.0 ± 0.2** |
| Leukocytes, 10$^9$/l | 9.2 ± 0.35 | 4.6 ± 0.19** | 5.7 ± 0.22** | 5.9 ± 0.26** | 5.6 ± 0.22** | 10.7 ± 0.19** |
| Segmented neutrophils, % | 16 ± 2.5** | 14.3 ± 1.6** | 13.3 ± 1.9** | 14.9 ± 2.6** | 20.3 ± 2.4** | 26 ± 2.2** |
| Lymphocytes, % | 75.5 ± 1.4 | 73.4 ± 1.8 | 72.1 ± 1.6 | 69.3 ± 0.9 | 72.5 ± 1.4 | 73.4 ± 1.1 |

*p 0.05 - in comparison with the biological control;
**p 0.05 - in comparison with the cyclophosphane control The combined use of a binuclear coordination compound of a d-metal with an aliphatic thiol and a hemostimulating means thus makes it possible to secure the therapeutic effect of the latter in physiologically more adequate doses.

Example No. 13

The effect of a coordination compound of palladium with acetylcysteine on the hypoglycemizing action of a preparation of thioctic acid with acetylcysteine (see Example No. 7).

An acetylcysteine-thioctic acid composition (see Example No. 7) was used as the test preparation.

Preparation of Solutions of the Test Compounds for Performance of the Study.

The white crystalline substances were stored at 4° C.; a substance was dissolved in physiological saline immediately before commencing an experiment. The solution was sterilized by passing through 0.22 μm Millex-GS (Millipore) filters in a sterile laminar-flow cabinet. In order to determine hypoglycemic action, the test substances were administered to fasting mice intravenously in physiological saline, thioctic acid in a dose of 100 mg/kg and 200 mg/kg, and thioctic acid combined with the coordination compound in an excess of ligand (equimolar ratio of thioctic acid and excess of ligand) in a dose of 10 and 20 mg/kg.

Performance of the Study.

Officially recommended tests [13, 14] were used to assess the sugar-reducing activity of the preparation:

the hypoglycemic test (reduction in the content of blood sugar in intact animals);

the glucose loading test (reduction in the sugar content in animals with hyperglycemia, caused by administration of glucose when fasting);

the alloxan diabetes model (reduction in the sugar content in the conditions of experimental chronic insulin insufficiency).

Blood was obtained after 1 h by caudal vein puncture and the serum glucose level was determined by the ortho-toluidine method.

Experiments to study the effect of the test substances on the blood glucose level were carried out on white mice weighing 17-18 g. The animals were deprived of food from the evening prior to the experiment. In the morning, the fasting mice were injected subcutaneously with 10% glucose solution at a rate of 1 g/kg (0.1 ml/10 g of body weight) [4]. Immediately after injecting the glucose, the experimental animals were injected subcutaneously with a reference preparation (insulin in a dose of 0.3 units/kg). The test substances were injected intramuscularly: thioctic acid at 5.5, 11, 100 and 200 mg/kg (the first two doses correspond to the content of thioctic acid in a composite with the coordination compound); thioctic acid in combination with the coordination compound in an excess of ligand—thioctic acid+CC—10 and 20 mg/kg. The blood glucose level was determined over a period of 4 hours with intervals of 1 hour.

The alloxan diabetes model was used in another series of experiments. Alloxan diabetes was induced by a single subcutaneous injection of alloxan hydrate (Chemapol, Czech Republic) in a dose of 100 mg/kg in rats weighing 180-200 g which had fasted for 24 hours. The following groups of animals were studied: intact rats, untreated rats with diabetes, and animals with diabetes which were given thioctic acid daily for 1 month in a dose of 100 mg/kg, and thioctic acid in combination with the coordination compound in a dose of 10 mg/kg intragastrically once daily. Administration of the preparations commenced after 7 days, when the blood glucose level had roughly doubled as compared with the control. Each group contained 20 animals of both sexes. The general condition of the animals, the demand for food and water, the body weight, and the blood serum levels of glucose, total lipids, triglycerides, lipoproteins and cholesterol were recorded in the course of the experiment.

Results of the Study.

The effect of the test compounds on the blood glucose level of the animals after glucose loading is shown in Table 8

TABLE 8

Blood sugar level of mice (mmol/l, M ± m) in the glucose loading test

| Preparation | Time after administration | | | |
|---|---|---|---|---|
| | 1 hour | 2 hours | 3 hours | 4 hours |
| Control | 4.2 ± 0.2 | 4.1 ± 0.2 | 4.3 ± 0.3 | 4.2 ± 0.1 |
| Thioctic acid + CC, (10 mg/kg) | 3.6 ± 0.3 | 2.9 ± 0.1 | 3.0 ± 0.2 | 3.2 ± 0.2 |
| Thioctic acid + CC (20 mg/kg) | 2.9 ± 0.2 | 2.4 ± 0.1 | 3.0 ± 0.1 | 3.1 ± 0.2 |
| Insulin | 1.2 ± 0.1 | 1.4 ± 0.1 | 1.6 ± 0.2 | 2.0 ± 0.1 |
| Thioctic acid 5.5 mg/kg | 4.3 ± 0.2 | 4.0 ± 0.2 | 4.4 ± 0.3 | 4.1 ± 0.1 |
| Thioctic acid 11 mg/kg | 4.5 ± 0.2 | 4.2 ± 0.2 | 4.2 ± 0.3 | 4.2 ± 0.1 |
| Thioctic acid 100 mg/kg | 3.0 ± 0.3 | 2.8 ± 0.1 | 2.5 ± 0.1 | 2.4 ± 0.3 |
| Thioctic acid 200 mg/kg | 2.7 ± 0.2 | 2.6 ± 0.3 | 2.3 ± 0.2 | 2.1 ± 0.2 |

The results of the study demonstrate the comparability of the effects of thioctic acid on blood sugar level in a dose of 100 and 200 mg/kg and of thioctic acid as part of a composite in a dose of 5.5 and 11 mg/kg. Without the coordination compound, thioctic acid did not exhibit a hypoglycemizing effect in doses of 5.5 and 11 mg/kg.

Extrapolating to rats, it could be assumed that the effective single dose would be 20 mg/kg of a composite of thioctic acid and the coordination compound and 200 mg/kg of thioctic acid administered alone. These doses were thus chosen for the treatment of experimental diabetes in rats, the results of which are presented in Table 9.

TABLE 9

Integral indices, indices of carbohydrate and lipid metabolism in white rats with experimental diabetes (M ± m)

| Indices | Experimental groups of animals | | | |
|---|---|---|---|---|
| | Intact | Diabetes | Diabetes + thioctic acid + CC | Diabetes + thioctic acid |
| 14 days | | | | |
| Percent living | 100 | 70 | 100 | 100 |
| Body weight, g | 190 ± 10 | 170 ± 10 | 185 ± 5 | 180 ± 10 |
| Daily water consumption | 15 ± 1 | 35 ± 2 | 25 ± 3 | 25 ± 5 |
| Glucose, mmol/l | 4.5 ± 0.3 | 16.2 ± 0.5 | 6.6 ± 0.3 | 5.2 ± 0.2 |
| Total lipids, g/l | 10.2 ± 0.3 | 17.4 ± 1.2 | 10.6 ± 0.6 | 10.4 ± 0.5 |
| Cholesterol, mmol/l | 1.4 ± 0.3 | 7.2 ± 0.2 | 2.6 ± 0.3 | 2.4 ± 0.2 |
| Triglycerides, mmol/l | 2.5 ± 0.2 | 2.8 ± 0.4 | 2.6 ± 0.1 | 2.3 ± 0.2 |
| β-lipoproteins, g/l | 2.0 ± 0.3 | 2.5 ± 0.1 | 2.2 ± 0.3 | 2.1 ± 0.2 |
| 20 days | | | | |
| Percent living | 100 | 50 | 100 | 100 |
| Body weight, g | 195 ± 10 | 165 ± 10 | 190 ± 5 | 185 ± 10 |
| Daily water consumption | 17 ± 2 | 45 ± 2 | 26 ± 3 | 25 ± 5 |
| Glucose, mmol/l | 4.2 ± 0.2 | 18.6 ± 1.2 | 6.4 ± 0.2 | 4.8 ± 0.1 |
| Total lipids, g/l | 10.1 ± 0.3 | 18.5 ± 1.3 | 11.6 ± 1.2 | 10.2 ± 0.3 |
| Cholesterol, mmol/l | 1.2 ± 0.2 | 7.6 ± 0.3 | 1.7 ± 0.3 | 1.4 ± 0.2 |
| Triglycerides, mmol/l | 2.5 ± 0.2 | 2.9 ± 0.4 | 1.6 ± 0.1 | 1.5 ± 0.2 |
| β-lipoproteins, g/l | 2.1 ± 0.3 | 2.6 ± 0.1 | 2.1 ± 0.3 | 2.1 ± 0.3 |
| 30 days | | | | |
| Percent living | 100 | 25 | 100 | 100 |
| Body weight, g | 200 ± 15 | 160 ± 10 | 195 ± 5 | 195 ± 10 |
| Daily water consumption | 18 ± 2 | 60 ± 5 | 23 ± 3 | 20 ± 3 |
| Glucose, mmol/l | 4.3 ± 0.1 | 17.5 ± 1.5 | 5.4 ± 0.3 | 4.6 ± 0.2 |
| Total lipids g/l | 9.8 ± 0.2 | 19.3 ± 0.8 | 10.5 ± 1.5 | 9.5 ± 0.2 |
| Cholesterol, mmol/l | 1.3 ± 0.3 | 8.2 ± 0.2 | 1.5 ± 0.2 | 1.4 ± 0.1 |
| Triglycerides, mmol/l | 2.3 ± 0.1 | 3.0 ± 0.2 | 1.5 ± 0.2 | 1.4 ± 0.2 |
| β-lipoproteins, g/l | 2.0 ± 0.3 | 2.5 ± 0.1 | 2.1 ± 0.1 | 2.1 ± 0.3 |

The results obtained testify that the composite of thioctic acid and the coordination compound exerts a good therapeutic effect in diabetes of moderate severity, the effect of the preparation being comparable to the effect of thioctic acid administered independently in a dose twenty times greater than the amount thereof in the composite. A fall in blood glucose level and normalization of the lipid metabolism indices was observed in all animals which received the thioctic acid composite. These animals gained weight normally, and their water consumption did not differ from the control group.

The composite of thioctic acid and the coordination compound thus has reasonable antidiabetic activity and normalizes the carbohydrate and lipid metabolism indices, which is manifested in a statistically reliable reduction in the blood cholesterol level of the experimental animals.

The use of thioctic acid in combination with the coordination compound of palladium with acetylcysteine in an excess of acetylcysteine (Example No. 7), in which the coordination compound of palladium with acetylcysteine was used in ultra-small amounts, facilitated expression of the hypoglycemizing effect of thioctic acid used in a dose which possesses no significant hypoglycemizing effect.

The combined use of a binuclear coordination compound of d-metal with an aliphatic thiol and a hypoglycemizing means thus makes it possible to secure the therapeutic effect of the latter in physiologically adequate doses.

Example No. 14

The effect of a coordination compound of palladium with acetylcysteine on the cardioprotective activity of adenosine A composition of a coordination compound of palladium in an excess of acetylcysteine and adenosine (acetylcysteine-adenosine (equimolar ratio) (see Example No. 8) was used as the test preparation.

Adenosine is one of the compounds capable of exerting a marked cardioprotective effect in myocardial ischemia, which has been demonstrated in various experimental models. Adenosine, which is a natural metabolite of the body, is an endogenous purine nucleoside. Adenosine modulates many physiological processes, particularly in the heart and the coronary vessels, but is used as a therapeutic preparation for the treatment of several types of arrhythmias [1]. The wide utilization of adenosine in the treatment of diseases of the heart with myocardial ischemia is hindered, among other reasons, as a consequence of the instability of the effect, and the rapid formation of tolerance to the action of the substance [15]. In myocardial ischemia, the administration of adenosine induces the onset of tachyphylaxis, i.e. a rapid and progressive decrease in the therapeutic effect, in relation to the cardioprotective effect of adenosine [16]. However, resistance to ischemia was maintained for several weeks when the cardioprotective effect of adenosine was present. Attempts to achieve a controllable stable prolonged effect of adenosine have not so far been crowned with success, which restricts its wide utilization as a means for the prophylaxis and treatment of myocardial affections in chronic ischemia and leaves it in the group of prospective drugs awaiting appropriate pharmacological solutions [17, 18].

Preparation of Solutions of the Test Compounds for Performance of the Study

The white crystalline substances were stored at 4° C.; a substance was dissolved in physiological saline immediately before commencing an experiment. The solution was sterilized by passing through 0.22 μm Millex-GS (Millipore) filters in a sterile laminar-flow cabinet. In order to study the cardioprotective effect, the test substances were administered to rats in physiological saline: adenosine in a dose not eliciting a cardioprotective effect, established in the course of the experiments; adenosine in combination with a coordination compound in excess ligand (equimolar ratio: adenosine—excess ligand); the amount of adenosine corresponded to a value established empirically in the course of the experiments.

Modeling Regional Ischemia-Reperfusion of the Myocardium in Anesthetized Animals In Vivo The experiments were performed on male Wistar rats weighing 200-300 g (RAMN Rappolovo Breeding Centre, St. Petersburg) and male C57B mice weighing 25-30 g (B&K, Sollentuna, Sweden). The animals were maintained in a 12/12-hour light regime and received standard feed and drinking water ad libitum. All the experiments were conducted in accordance with the "Handbook on the care and use of laboratory animals" (USA National Institute of Health publication No. 85-23) and "Handbook on the experimental (preclinical) study of new pharmacological substances".

Initial anesthesia of rats was performed by intraperitoneal administration of etaminal sodium (Nembutal) in a single dose of 7 mg/100 g. The experiments were performed with artificial ventilation of the lungs AVL) via a tracheotomy (respiration rate—60/min, respiratory volume—3 ml/100 g of body weight). AVL was carried out with room air using a Vita-1 unit (PO Krasnogvardeyets, St. Petersburg). A breathing valve for small laboratory animals was used, allowing the dead space volume of the apparatus to be reduced and limiting accumulation of carbon dioxide in the flow system of the apparatus. Arterial pressure (AP) was measured during the experiment using a miniature pressure sensor (Baxter, USA) via a heparinized catheter inserted into the left common carotid artery. A median skin incision was made in the neck, with subsequent blunt separation of the tissues with forceps, for access to the trachea and carotid artery. An electrocardiogram (ECG) was recorded in the course of the experiment (Kardiotekhnika-EKG-8, ZAO Inkart, St. Petersburg) with standard leads, using subcutaneous needle electrodes 2 mm in diameter and 25 mm long. At the start of the experiment, the left femoral vein was catheterized for intravenous infusion of Nembutal with the object of maintaining anesthesia and also for the administration of test preparations and, at the end of the experiment, Evans blue.

A previously described method [19] was used to model ischemia-reperfusion of the myocardium. The heart was accessed via a thoracotomy in the fourth intercostal on the left. An L-shaped skin incision was made first, then the large and small pectoral muscles were separated layer by layer with an electrocoagulator, after which the intercostal muscles were separated and the pleura was exposed. The pericardium was then opened by a blunt method and, using the medial edge of the auricula of the left atrium on the left, and the cone of the pulmonary artery on the right, for guidance the location of the common trunk of the LCA was determined, and a polypropylene ligature for this was placed with the aid of an atraumatic needle (6-O, Cardiopoint, CV-301). Removal of the heart from the wound was avoided since, apart from causing mechanical trauma to the heart, such a manipulation inevitably leads to serious disturbances to the hemodynamics.

An occluder was formed in order to create reversible ischemia of the myocardium: the ends of the ligature surrounding the coronary artery were led into the interior of a polyethylene tube 1 mm in diameter and 5-6 cm long (PE 40), after which occlusion of the left coronary artery (LCA) was achieved by moving the tube towards the heart, and reperfusion by moving it in the opposite direction. A clamp was applied to the tube with the object of maintaining occlusion for 30 minutes. The animals were located on a thermostatted operating table during the experiment; during this time, the body temperature of the animal was maintained in the range 37.5±0.5° C.

The onset of myocardial ischemia was confirmed by the presence of a transitory fall in arterial pressure (AP), and also the occurrence of regional cyanosis, ischemic changes on the ECG (elevation of the ST segment) and, sometimes, systolic protrusion of the wall of the left ventricle (LV).

30-minute occlusion of the LCA with subsequent 90-minute reperfusion was used to create irreversible ischemic-reperfusion damage to the myocardium, which is a test for assessing cardioprotective effects.

Method for Determining the Size of an Experimental Myocardial Infarct

The generally accepted differential indicator method, which allows the irreversibly damaged (necrotized) myocardial tissue to be distinguished from the tissue which has retained viability within the limits of a zone of the heart which has been subjected to ischemia, was used to determine the size of the MI in experiments with regional ischemia in vivo. The substance of this method is as follows. In the first stage of staining after completing the physiological part of the experiment, the ligature was again tightened around the coronary artery and a bolus of 0.5 ml of 5% Evans Blue solution (MP Biomedicals, USA) was injected intravenously. Entering the sections of the heart supplied with blood and vascularized primarily by the right coronary artery, the dye stained them dark blue, while the basin of the occluded LCA remained unstained. After visualizing the boundary between the blood-supplied and ischemic sections, the heart was rapidly cut out, thoroughly washed with physiological saline and, after removing the major vessels and atria, was cut transversely into five fragments (slices) of identical thickness (2 mm). The basal surfaces of the heart slices were photographed with an Olympus 2020 digital camera combined with a stereomicroscope (MBS-10, LOMO, St. Petersburg) by means of a microphotographic device (MPD). In order to avoid the formation of spots of light, the slices were placed for photography in a low bottle filled with physiological saline such that the liquid covered the basal surface of the slice.

Computer processing of the images was performed using specially developed software ("Automation of microscopic analysis in the field of medicine (LittleMed)", certificate of official registration of a computer program No. 2003611599). The relative size of the anatomical risk zone for a particular heart was obtained by calculating the arithmetical mean of the values computed for each of the 5 slices. For each slice, the size of the risk zone was expressed as a percentage by dividing the area of the Evans-negative sectors by the total area of the slice and multiplying by 100. Experiments in which the relative volume of the risk zone was less than 15% of the total volume of the heart were excluded from the series.

In the second stage of staining, slices of myocardium were placed in a 1% solution of 1,2,3-triphenyltetrazolium chloride (TTC, MP Biomedicals, USA), which stains viable tissue with preserved activity of NAD-dependent enzymes bright red (brick red). The slices were incubated for 15 minutes at a temperature of 37° C. and pH 7.4. After incubation of the slices with TTC within the boundaries of the anatomical risk zone, sectors of brick-red color and sectors with the native color of the myocardium were determined. The basal surfaces of the slices were photographed again and, processing the resultant images by the method indicated above, the relative size of the infarct was calculated as the ratio of the size of the risk zone to the size of the infarct zone (in percent). In a number of cases, additional incubation of slices in 10% neutral formalin solution was employed before photographing for better demarcation of the infarct zone from tissue with preserved viability after staining the slices with TTC.
Computer Processing of Data and Statistical Analysis Methods.

The statistical reliability of the differences in the sizes of the anatomical risk zone and the infarct zone was assessed using the SPSS software package (ANOVA, Scheffe test). The results were expressed in the "average±standard deviation" form. Values of P less than 0.05 were regarded as reliable.
Results of Determining the Effectiveness of Protecting the Myocardium Against Necrosis Using the Test Preparation Pharmacological protection of the myocardium against necrosis was performed using an acetylcysteine (aC)—adenosine (equimolar ratio) composition containing a coordination compound of palladium with an aliphatic thiol—acetylcysteine, with a coordination compound—acetylcysteine ratio of 1:1000.

In order to determine the minimum effective concentrations of the test composition, experiments were set up permitting determination of the concentration of adenosine in which it exerted no cardioprotective effect or manifested this to an insignificant extent, corresponding to the minimal level of myocardial protection against necrosis by the corresponding regime of brief ischemia with subsequent reperfusion. The cardioprotective effect of the acetylcysteine containing the coordination compound of palladium was determined in another series of experiments. The concentrations of acetylcysteine administered to the animals were equimolar with the concentrations of adenosine in which it did not exert a cardioprotective effect. The acetylcysteine (aC)—adenosine (equimolar ratio) composition, including the coordination compound of palladium, was used in subsequent experiments in concentrations in which the substances forming it did not exert a cardioprotective effect and concentrations in which it was manifested.

The following groups were used in order to determine the dose of adenosine which did not exert a cardioprotective effect, i.e. which did not protect the myocardium against necrosis when carrying out ischemia and subsequent reperfusion:

1. Control (n=12). In this group, the LCA was occluded for 30 minutes with subsequent 90-minute reperfusion and without other interventions. 30 minutes before coronary occlusion, physiological saline (0.9% solution of sodium chloride in distilled water) was injected intravenously in a volume of 2 ml at a rate of 0.5 ml/min;
2. Group No. 1 (n=10). Modeling of myocardial infarct was preceded by intravenous infusion of adenosine in a dose of 0.1 μmol/kg (in groups 1-9, the infusion volume averaged 2 ml, the infusion rate was 0.5 ml/min, and administration was performed 30 minutes before coronary occlusion);
3. Group 2 (n=14). Modeling of myocardial infarct was preceded by intravenous infusion of adenosine in a dose of 0.25 μmol/kg;
4. Group 3 (n=9). Modeling of myocardial infarct was preceded by intravenous infusion of adenosine in a dose of 0.5 μmol/kg;
5. Group 4 (n=8). Modeling of myocardial infarct was preceded by intravenous infusion of adenosine in a dose of 1.0 μmol/kg;
6. Group 5 (n=8). Modeling of myocardial infarct was preceded by intravenous infusion of adenosine in a dose of 2.5 μmol/kg;
7. Group 6 (n=10). Modeling of myocardial infarct was preceded by intravenous infusion of adenosine in a dose of 5.0 μmol/kg;
8. Group 7 (n=11). Modeling of myocardial infarct was preceded by intravenous infusion of adenosine in a dose of 10.0 μmol/kg;
9. Group 8 (n=11). Modeling of myocardial infarct was preceded by intravenous infusion of adenosine in a dose of 25.0 μmol/kg;
10. Group 9 (n=10). Modeling of myocardial infarct was preceded by intravenous infusion of adenosine in a dose of 50.0 μmol/kg.

The size of the infarct zone in group No. 1 (control) was 63.8±3.32% of the size of the anatomical risk zone. While there were no differences in the size of the infarct zone in groups No. 1-5 as compared to the control—64.7±3.47%, 63.1±4.31%, 62.7±4.11%, 65.1±4.84% and 60.9±5.10% respectively in group order, in groups 6-9 the size of the infarct zone was reduced by a factor of approximately 1.5-2.5 as compared with the control and was 35.9±3.59%, 32.7±3.21%, 28.2±3.43%, and 26.5±2.87% respectively. The doses of adenosine which did not lead to protection of the myocardium against ischemia and which were accompanied by a reduction in the zone of necrosis by a factor of 1.5-2.5 were thus established in the course of the experiments performed. The increment in the effect with increase in the concentration of adenosine indicates the existence of a cardioprotective effect of the preparation. The overall cardioprotective effect is made up of the receptor-mediated effect of adenosine on individual cells. The presence of an adequate number of receptors at each cell, capable of initiating a cellular signal of specific strength and duration, will determine the ability of adenosine to initiate a complex of cytoprotective reactions. The results obtained, showing a relatively weak increase in the cardioprotective effect of adenosine on multiple increase in the concentration thereof administered, may indicate the inability of the adenosine receptors of a significant part of the cells to react with their ligand. Taking into account the ability of coordination compounds to convert cellular receptors superficially into a conformation capable of reacting with the ligand, the possibility of potentiating the cardioprotective effect of adenosine by the combined administration thereof with a coordination compound must be anticipated. In performing the experiments, account was taken of the presence of endogenous adenosine, which also has cytoprotective effects in unfavorable circumstances. In this case also, the possibilities of a cardioprotective effect thereof are limited by the number of interacting receptors present on a cell. In this connection, the concentrations of coordination compound for which a cardioprotective effect was lacking were determined.

The ability of a coordination compound of palladium, administered in an excess of acetylcysteine with a coordination compound to acetylcysteine ratio of 1:1000, to exert a cardioprotective effect was determined in a series of experiments. The concentrations of acetylcysteine in the experiment corresponded to those of adenosine in which the latter lacked a cardioprotective effect.

The following groups were used in the study:
1. Control (n=14). In this group, the LCA was occluded for 30 minutes with subsequent 90-minute reperfusion and without other interventions. 30 minutes before coronary occlusion, physiological saline (0.9% solution of sodium chloride in distilled water) was injected intravenously in a volume of 2 ml at a rate of 0.5 ml/min;
2. Group No. 1 (n=9). Modeling of myocardial infarct was preceded by intravenous infusion of acetylcysteine containing a coordination compound of palladium with acetylcysteine in a coordination compound:acetylcysteine ratio of 1:1000 (hereinafter in the text—the agent). The agent was administered in an amount of 0.1 µmol/kg (in groups 1-5, the infusion volume averaged 2 ml, the infusion rate was 0.5 ml/min, and administration was performed 30 minutes before coronary occlusion);
3. Group 2 (n=10). Modeling of myocardial infarct was preceded by intravenous infusion of the agent, which was administered in an amount of 0.25 µmol/kg;
4. Group 3 (n=9). Modeling of myocardial infarct was preceded by intravenous infusion of the agent, which was administered in an amount of 0.5 µmol/kg;
5. Group 4 (n=11). Modeling of myocardial infarct was preceded by intravenous infusion of the agent, which was administered in an amount of 1.0 µmol/kg;
6. Group 5 (n=7). Modeling of myocardial infarct was preceded by intravenous infusion of the agent, which was administered in an amount of 2.5 µmol/kg;
7. Group 6 (n=10). Modeling of myocardial infarct was preceded by intravenous infusion of the agent, which was administered in an amount of 5.0 µmol/kg;

The size of the infarct zone in the control was 71.8±6.17% of the size of the anatomical risk zone. In groups No. 1-4, no differences whatever were found in the size of the infarct zone as compared with the control—74.2±6.94%, 74.2±6.61%, 72.6±7.01%, 70.1±6.34%. In groups No. 5 and No. 6, the cardioprotective effect of the agent administered was manifested in an approximately 2.0-fold reduction in the infarct zone compared with the control—41.7±3.12% and 34.4±4.65% respectively in group order.

The amounts of the agent exerting a cardioprotective effect, expressed in a two-fold reduction of the infarct zone and conversely not protecting the myocardium against ischemia, were thus determined in the course of the experiments performed.

The ability of a preparation comprising adenosine and acetylcysteine in equimolar ratio and a coordination compound of palladium with acetylcysteine (the ratio of coordination compound to acetylcysteine was 1:1000) to exert a cardioprotective effect was assessed in a subsequent series of experiments. In accordance with the results of the previous experiments, a study was made of preparations containing adenosine and acetylcysteine+a coordination compound of palladium with acetylcysteine (the ratio of coordination compound to acetylcysteine was 1:1000) and administered in amounts where a cardioprotective effect was not manifested—preparation No. 1 in which the amounts of adenosine and acetylcysteine+a coordination compound of palladium and acetylcysteine (the ratio of coordination compound to acetylcysteine was 1:1000) administered were 0.5 µmol/kg of each, and preparation No. 2 in which the amounts of adenosine and acetylcysteine+a coordination compound of palladium and acetylcysteine (the ratio of coordination compound to acetylcysteine was 1:1000) administered were 1.0 µmol/kg of each. Preparation No. 3 in which the amounts of adenosine and acetylcysteine+a coordination compound of palladium and acetylcysteine (the ratio of coordination compound to acetylcysteine was 1:1000) administered were 2.5 µmol/kg of each. Preparation No. 4 in which the amounts of adenosine and acetylcysteine+a coordination compound of palladium and acetylcysteine (the ratio of coordination compound to acetylcysteine was 1:1000) administered were 5.0 µmol/kg of each.

1. Control (n=14). In this group, the LCA was occluded for 30 minutes with subsequent 90-minute reperfusion and without other interventions. 30 minutes before coronary occlusion, physiological saline (0.9% solution of sodium chloride in distilled water) was injected intravenously in a volume of 2 ml at a rate of 0.5 ml/min;
2. Group 1 (n=14). Modeling of myocardial infarct was preceded by intravenous infusion of preparation No. 1 (in groups 1-4, the infusion volume averaged 2 ml, the infusion rate was 0.5 ml/min, and administration was performed 30 minutes before coronary occlusion);
3. Group 2 (n=11). Modeling of myocardial infarct was preceded by intravenous infusion of preparation No. 2.
4. Group 3 (n=15). Modeling of myocardial infarct was preceded by intravenous infusion of preparation No. 3.
5. Group 4 (n=12). Modeling of myocardial infarct was preceded by intravenous infusion of preparation No. 4.

The size of the infarct zone in the control was 79.3±6.22% of the size of the anatomical risk zone. In group No. 1 there were no reliable differences in the size of the infarct zone compared with the control—75.6±6.85%. In groups No. 2, No. 3 and No. 4, the size of the infarct zone compared with the control was 46.3±4.71%; 29.76±2.97% and 11.8±3.12% respectively (P<0.05). The combined administration of a coordination compound of palladium with acetylcysteine as part of preparation No. 2 allowed the cardioprotective effect of adenosine to be manifested, which led to a virtually two-fold reduction in the infarct zone during ischemia as compared with the control. Increasing the amounts of adenosine and the coordination compound of palladium with acetylcysteine administered facilitated greater expression of the cardioprotective effect. Preparation No. 3 provided a 2.5-fold reduction of the infarct zone as compared with the control. Preparation No. 4 produced the most pronounced cardioprotective effect, providing a 6.5-fold reduction in the infarct zone as compared with the control. Preparation No. 4 comprised amounts of adenosine and the coordination compound of palladium with acetylcysteine which when used alone gave a less significant cardioprotective effect. The mechanism of the development of the resistance of each individual myocardial cell to ischemia is the same and is initiated after generating a regulatory signal of predetermined strength and length [15, 16]. In this connection, reduction of the infarct zone testifies to increase in the number of cells resistant to prolonged ischemia. The use of adenosine alone in significantly larger amounts gave a less pronounced cardioprotective effect in prolonged ischemia. Among other things, this result shows that the amount of adenosine was sufficient to provide a more pronounced cardioprotective effect, but the ability of adenosine receptors to interact therewith was, for whatever reason, limited, leading to the result obtained. The combined administration of adenosine and the coordination compound of palladium with acetylcysteine facilitated implementation of the cardioprotective effect of smaller amounts of the preparation by increasing its therapeutic effectiveness. No disturbances of the heart rhythm or stopping of the heart, which are the most undesirable complications of work with the preparation, were observed in the course of the experiments with administration of adenosine. It must be noted that the amounts of adenosine administered were close to those values which are found during protection of the myocardium against prolonged ischemia by brief episodes of ischemia and reperfusion and are considered physiological [15, 16].

The combined use of ultra-small concentrations of a coordination compound of an aliphatic thiol in an excess of ligand and physiologically acceptable concentrations of a pharmacologically active substance—adenosine, has thus demonstrated the therapeutic effect of adenosine in physiologically adequate doses.

BIBLIOGRAPHY

1. Basic & Clinical Pharmacology. Edited by Bertram G. Katzung, M D, PhD, 1995.
2. Bogatyreva N. S., Finkelstein A. V., Galsitskaya O. V. Trend of amino acid compositions of different taxa//J. Bioinf. Comput. Biol., 2006, Vol. 4, pp. 597-608
3. Jeffry C. J Moonlighting proteins//TIBS, 1999, pp. 8-11.
4. Stavrovskaya A. A., Stromskaya T. P. ABC family transporter proteins and multiple drug resistance of tumor cells// Biokhimiya, 2008, Vol. 73, No. 5, pp. 735-750.
5. Bridges A. J. The rationale and strategy used to develop a series of highly potent, irreversible, inhibitors of the epidermal growth factor receptor family of tyrosine kinases// Curr. Med. Chem., 1999, 6, 825-843.
6. Modjtahedi H., Dean Ch. The receptor for epidermal growth factor and ligands: expression, prognostic value and target for therapy in cancer//Intern. J. Oncol., 1995, Vol. 4, pp. 277-296.
7. Townsend D. M., He L., Hutchens S., et al. NOV-002, a Glutathione Disulfide Mimetic, as a Modulator of Cellular Redox Balance//Cancer Res., 2008, Vol. 68, pp. 2870-2877.
8. Steinberg T. H. Cellular transport of drugs//Clin. Infect. Dis., 1994, Vol. 19. No. 5, pp. 916-921.
9. Scotto K. W. Transcriptional regulation of ABC drag transporters//Oncogene, 2003, Vol. 22, No. 47, pp. 7496-7511.
10. Alberts B., Johnson A., Lewis J., Raff M., Roberts K., Walter P. Molecular biology of the cell, 4th ed. N.Y., Garland Science, Taylor and Francis group. 2002, 1616 pp.
11. Kelly C. P., Cramer C. J., Truhlar D. G. Adding Explicit Solvent Molecules to Continuum Solvent Calculations for the Calculation of Aqueous Acid Dissociation Constants// J. Phys. Chem. A., 2006, 110(7), 2493-2499.
12. Saracino G. A., Improta R., Barone V. Absolute pKa determination for carboxylic acids using density functional theory and the polarizable continuum model//Chem. Phys. Lett., 2003, 373(3-4), 411-415.
13. Methodological recommendations for experimental investigation of new peroral hypoglycemic pharmaceuticals. In: Leading methodological papers on the experimental and clinical investigation of drugs. Part 6. Moscow, 1986, p. 202.
14. Handbook of experimental (preclinical) investigation of new pharmacological substances. Ed. Khabriyev R. U. 2nd ed. Moscow, Izd. Meditsina, 2005, 832 pp.
15. Yellon D. M., Downey J. M. Preconditioning the myocardium: from cellular physiology to clinical cardiology// Physiol. Rev., 2003, Vol. 83, No. 4, pp. 1113-1151.
16. Tsuchida A., Thompson R., Olsson R. A., Downey J. M. The anti-infarct effect of an adenosine $A_1$-selective agonist is diminished after prolonged infusion as is the cardioprotective effect of ischemic preconditioning in rabbit heart//J. Mol. Cell. Cardiol., 1994, Vol. 26, No. 3, pp. 303-311.
17. Dana A., Baxter G., Walker J. M., Yellon D. M. Prolonging the delayed phase of myocardial protection: repetitive adenosine $A_1$ receptor activation maintains rabbit myocardium in a preconditioned state//J. Am. Coll. Cardiol., 1998, Vol. 31, No. 5, pp. 1142-1149.
18. Downey J. M., Cohen M. V. Reducing infarct size in the setting of acute myocardial infarction//Prog. Cardiovasc. Dis. 2006, Vol. 48, No. 5, pp. 363-371.
19. Selye H., Bajusz E., Grasso S., Mendell P. Simple techniques for the surgical occlusion of coronary vessels in the rat//Angiology, 1960, Vol. 11, No. 5, pp. 398-407.
20. Leiris J., Harding D. P., Pestre S. The isolated rat heart: a model for studying myocardial hypoxia or ischemia//Basic Res. Cardiol., 1984, Vol. 79, No. 3. pp. 315-323.
21. Himory N., Matsuura A. A simple technique for occlusion and reperfusion of coronary artery in conscious rats//Am. J. Physiol., 1989, Vol. 256, pp. H1719-H1725.
22. Sutherland F. J., Hearse D. J. The isolated blood and perfusion fluid perfused heart//Pharmacol. Res., 2000, Vol. 41, No. 6, pp. 613-627.

The invention claimed is:

1. A compound of the general formula

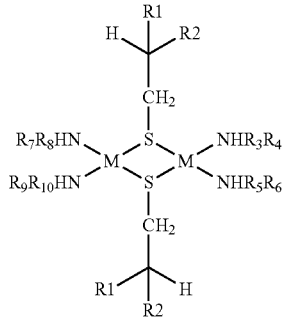

or a pharmaceutically acceptable salts thereof,
where M signifies metal atoms selected independently from the group consisting of Pd, Fe, Mn, Co, Ni, Cu, Zn and Mo,
$R^1$ and $R^2$, independently of each other, signify hydrogen, amino, hydroxy, carboxy, cyano, $C_{1-12}$alkyl, $C_{2-12}$alkenyl, $C_{2-12}$alkynyl, $C_{1-12}$alkoxy, $C_{1-12}$alkylamino, $C_{1-12}$alkoxycarbonyl, $C_{1-12}$alkylamido, arylamido, wherein the alkyl groupings included in said substituents may, in their turn, be substituted by one or more than one of the following groups: hydroxy, oxy, carboxy, amino, or amido, or $R^1$ and $R^2$, taken together, are oxo;
$R^3$-$R^{10}$, independently of each other, signify hydrogen, or $NHR^3R^4$ and $NHR^5R^6$, taken together, and/or $NHR^7R^8$ and $NHR^9R^{10}$, taken together, are a ligand (or ligands), containing one or several donor aliphatic or aromatic atoms of nitrogen and occupying the cis-position on the metal atoms (M).

2. The compound as claimed in claim 1, where $NHR^3R^4$ and $NHR^5R^6$, taken together, and/or $NHR^7R^8$ and $NHR^9R^{10}$, taken together, are a diamino compound or an aryl with two aromatic nitrogen atoms.

3. The compound as claimed in claim 2, where the diamino compound is a $C_2$-$C_6$ diaminoalkylene, and the aryl contains two pyridyl rings.

4. The compound as claimed in claim 3, where $NHR^3R^4$ and $NHR^5R^6$, taken together, and/or $NHR^7R^8$ and $NHR^9R^{10}$, taken together, are ethylenediamine, 2,2'-bidipyridyl (2,2'-bipy), 1,10-phenanthroline (1,10-phen), or derivatives thereof.

5. The compound as claimed in claim 3, where $R^1R^2CH$—$CH_2$—SH is 2-aminoethanethiol (aet, cysteamine), 2-acetamidoethanethiol, cysteine (Cys), cysteine methyl ester, cysteine ethyl ester, acetylcysteine (Accys), acetylcysteine methyl ester, acetylcysteine ethyl ester, acetylcysteine nitrile, 3-mercaptopropionic acid, γ-glutamine-cysteine-glycine, homocysteine, thioglycolic acid or derivatives thereof.

6. The compound as claimed in claim 3, where $NHR^3R^4$ and $NHR^5R^6$, taken together, and/or $NHR^7R^8$ and $NHR^9R^{10}$, taken together, are ethylenediamine, 2,2'-bidipyridyl (2,2'-bipy), 1,10-phenanthroline (1,10-phen), or derivatives thereof, and $R^1R^2CH$—$CH_2$—SH is 2-aminoethanethiol (aet, cysteamine), 2-acetamidoethanethiol, cysteine (Cys), cysteine methyl ester, cysteine ethyl ester, acetylcysteine (Accys), acetylcysteine methyl ester, acetylcysteine ethyl ester, acetylcysteine nitrile, 3-mercaptopropionic acid, γ-glutamine-cysteine-glycine, homocysteine, thioglycolic acid or derivatives thereof.

7. The compound as claimed in claim 1 with the formula

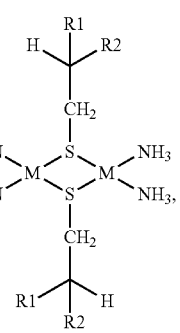

where M, $R^1$ and $R^2$ are as defined in claim 1.

8. The compound as claimed in claim 1, which is a compound selected from the group which consisting of [Pd$_2$(μ-S-L-Cys)(μ-S-L-CysH)(2,2'-dipy)$_2$](NO$_3$)$_3$.4.5H$_2$O, Pd$_2$(aetH)$_2$ (phen)$_2$](NO$_3$)$_4$. H$_2$O$_9$, [Pd$_2$(μ-S-Accys)$_2$(dipy)$_2$]Cl$_2$.H$_2$O, [Pd$_2$(μ-S-Accys)$_2$(NH$_3$)$_4$]Cl$_2$, and [Cu$_2$(μ-S-Cys)$_2$(dipy)$_2$]Cl$_2$.

9. The compound as claimed in claim 8, which is [Pd$_2$(μ-S-L-Cys)(μ-S-L-CysH)(2,2'-dipy)$_2$](NO$_3$)$_3$.4.5H$_2$O, which crystallizes in triclinic syngony with spatial group P-1, with elementary cell parameters (Å): a=13.86, b=13.82, c=12.17, α=122.13°, β=103.61°, γ=91.40°, V(Å$^3$)=1887.0, Z=1, characterized by an IR spectrum (KBr pellets), $v_{max}$, cm$^{-1}$: 419, 542,590,648,689,722, 765,807,977,1022,1036,1072, 1107,1164, 1174,1204,1226,1240, 1272,1312,1353, 1364,1384,1447, 1469,1563,1601, 1666,1728,3073,3108,3221,3283, 3427,3953.

10. The compound as claimed in claim 8, which is Pd$_2$(aetH)$_2$(phen)$_2$](NO$_3$)$_4$.H$_2$O, which crystallizes in monoclinic syngony with spatial group Cc, elementary cell parameters, Å: a=24.53, b=13.10, c=22.65, β=104.26°, V(Å$^3$)= 7052.25, Z=4.

11. The compound as claimed in claim 8, which is [Pd$_2$(μ-S-Accys)$_2$(dipy)$_2$]Cl$_2$.H$_2$O, characterized by an IR spectrum (KBr pellets), $v_{max}$, cm$^{-1}$: 507, 640, 692, 774, 815, 879, 946, 1058, 1094, 1212, 1229, 1343, 1381, 1404, 1427, 1573, 1723, 2655, 2820, 2971, 3377, 3406, 3480.

12. The compound as claimed in claim 8, which is [Pd$_2$(μ-S-Accys)$_2$(NH$_3$)$_4$]Cl$_2$, characterized by an IR spectrum (KBr pellets), $v_{max}$, cm$^{-1}$: 512, 597, 692, 773,839,879,946,1094, 1212,1229,1254,1343,1403,1521,1572,1594,1723,2655,2925, 2971,3119,3460.

13. The compound as claimed in claim 8, which is [Cu$_2$(μ-S-Cys)$_2$(dipy)$_2$]Cl$_2$, characterized by an IR spectrum (KBr pellets), $v_{max}$, cm$^{-1}$: 520, 691, 815, 879, 1058, 1133, 1212, 1229, 1254, 1343, 1404, 1572, 1594, 1627, 2655, 2925, 2940, 2971, 3119, 3480.

14. A pharmaceutical composition which comprises at least one compound as claimed in claim 1 in an effective amount together with pharmaceutically acceptable excipients.

15. The pharmaceutical composition of claim 14, wherein the pharmaceutical composition is formulated for external, inhalation, enteral and parenteral use.

16. The pharmaceutical composition as claimed in claim 14, which additionally contains free CHR$^1$R$^2$—CH$_2$SH, where R$^1$ and R$^2$ are as defined in claim 1.

17. The pharmaceutical composition as claimed in claim 14, which additionally contains thioctic acid.

18. The pharmaceutical composition as claimed in claim 14, which additionally contains lithium ions.

19. The pharmaceutical composition as claimed in claim 14, which additionally contains adenosine.

\* \* \* \* \*